(12) United States Patent
Chesonis et al.

(10) Patent No.: US 9,499,635 B2
(45) Date of Patent: *Nov. 22, 2016

(54) INTEGRATED WOOD PROCESSING AND SUGAR PRODUCTION

(71) Applicant: Sweetwater Energy, Inc., Rochester, NY (US)

(72) Inventors: Arunas Chesonis, Rochester, NY (US); Jerry W. Horton, Rush, NY (US)

(73) Assignee: Sweetwater Energy, Inc., Rochester, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/050,244

(22) Filed: Oct. 9, 2013

(65) Prior Publication Data

US 2014/0038244 A1  Feb. 6, 2014

Related U.S. Application Data

(63) Continuation-in-part of application No. 13/793,860, filed on Mar. 11, 2013, which is a continuation of application No. 13/646,425, filed on Oct. 5, 2012, now Pat. No. 8,426,161, which is a continuation of application No. 11/974,129, filed on Oct. 11, 2007, now Pat. No. 8,323,923.

(60) Provisional application No. 60/851,424, filed on Oct. 13, 2006, provisional application No. 61/711,588, filed on Oct. 9, 2012.

(51) Int. Cl.
| | |
|---|---|
| *C12P 19/00* | (2006.01) |
| *C12P 19/02* | (2006.01) |
| *C12P 19/04* | (2006.01) |
| *C12P 19/14* | (2006.01) |
| *C08B 1/00* | (2006.01) |
| *C12M 1/00* | (2006.01) |
| *C13K 1/02* | (2006.01) |
| *C12M 1/40* | (2006.01) |
| *C12M 1/33* | (2006.01) |

(52) U.S. Cl.
CPC ............ *C08B 1/003* (2013.01); *C12M 21/18* (2013.01); *C12M 43/02* (2013.01); *C12M 45/02* (2013.01); *C12P 19/02* (2013.01); *C12P 19/14* (2013.01); *C13K 1/02* (2013.01)

(58) Field of Classification Search
None
See application file for complete search history.

(56) References Cited

U.S. PATENT DOCUMENTS

| | | | |
|---|---|---|---|
| 3,563,799 A | 2/1971 | Zievers et al. | |
| 3,730,770 A | 5/1973 | Zievers et al. | |
| 4,048,341 A | 9/1977 | Lagerstrom et al. | |
| 4,070,232 A | 1/1978 | Funk | |
| 4,182,780 A | 1/1980 | Lagerstrom et al. | |
| 4,201,596 A | 5/1980 | Church et al. | |
| 4,237,226 A * | 12/1980 | Grethlein ........................ 435/99 |
| 4,288,551 A | 9/1981 | Gudnason et al. | |
| 4,326,032 A | 4/1982 | Grove | |
| 4,350,766 A | 9/1982 | Mehlberg | |
| 4,395,488 A | 7/1983 | Rowe | |
| 4,414,330 A | 11/1983 | Zucker et al. | |
| 4,447,534 A | 5/1984 | Moebus et al. | |
| 4,478,854 A | 10/1984 | Adler-nissen et al. | |
| 4,502,890 A | 3/1985 | Urbanic | |
| 4,520,105 A | 5/1985 | Sinner et al. | |
| 4,600,590 A | 7/1986 | Dale | |
| 4,612,286 A | 9/1986 | Sherman et al. | |
| 4,615,742 A | 10/1986 | Wright | |
| 4,644,060 A | 2/1987 | Chou | |
| 4,650,689 A | 3/1987 | Hedrick | |
| 4,806,475 A | 2/1989 | Gould | |
| 5,037,663 A | 8/1991 | Dale | |
| 5,144,008 A | 9/1992 | Ikeda et al. | |
| 5,171,592 A | 12/1992 | Holtzapple et al. | |
| 5,177,008 A | 1/1993 | Kampen | |
| 5,177,009 A | 1/1993 | Kampen | |
| 5,338,366 A | 8/1994 | Grace et al. | |
| 5,454,911 A | 10/1995 | Rafferty | |
| 5,473,061 A | 12/1995 | Bredereck et al. | |
| 5,693,296 A | 12/1997 | Holtzapple et al. | |
| 5,726,046 A | 3/1998 | Farone et al. | |
| 5,846,787 A | 12/1998 | Ladisch et al. | |
| 5,865,898 A | 2/1999 | Holtzapple et al. | |
| 5,916,780 A | 6/1999 | Foody et al. | |

(Continued)

FOREIGN PATENT DOCUMENTS

| | | |
|---|---|---|
| CA | 1267407 B | 4/1990 |
| EP | 0105937 B1 | 11/1987 |
| EP | 1259466 B1 | 10/2008 |
| EP | 1307735 B1 | 11/2008 |
| EP | 1299170 B1 | 8/2010 |

(Continued)

OTHER PUBLICATIONS

Woiciechowski et al. 2002. Acid and Enzymatic Hydrolysis to Recover Reducing Sugars from Cassava Bagasse: an Economic Study. Brazilian Archives of Biology and Technology, vol. 45, No. 3, pp. 393-400.*

(Continued)

*Primary Examiner* — Debbie K Ware
*Assistant Examiner* — Kailash C Srivastava
(74) *Attorney, Agent, or Firm* — Wilson Sonsini Goodrich & Rosati

(57) ABSTRACT

Provided is a system for localizing and optimizing harvesting of woody biomass by providing a plurality of portable pretreatment units at harvesting or mill sites. The sugars derived from woody waste products can be transported to plants for processing or processing directly by plants located at mill sites to generate biofuels and other chemicals.

7 Claims, 5 Drawing Sheets

(56) References Cited

U.S. PATENT DOCUMENTS

| | | | |
|---|---|---|---|
| 5,939,544 A | 8/1999 | Karstens et al. |
| 5,969,189 A | 10/1999 | Holtzapple et al. |
| 5,986,133 A | 11/1999 | Holtzapple et al. |
| 6,043,392 A | 3/2000 | Holtzapple et al. |
| 6,106,888 A | 8/2000 | Dale et al. |
| 6,176,176 B1 | 1/2001 | Dale et al. |
| 6,258,175 B1 | 7/2001 | Lightner |
| 6,262,313 B1 | 7/2001 | Holtzapple et al. |
| 6,332,542 B2 | 12/2001 | Bilodeau et al. |
| 6,365,732 B1 | 4/2002 | Van Thorre |
| 6,409,841 B1 * | 6/2002 | Lombard ............ C13K 1/02 127/36 |
| 6,416,621 B1 | 7/2002 | Karstens |
| 6,475,552 B1 | 11/2002 | Shah et al. |
| 6,478,965 B1 | 11/2002 | Holtzapple et al. |
| 6,509,180 B1 | 1/2003 | Verser et al. |
| 6,990,459 B2 | 1/2006 | Schneider |
| 7,109,005 B2 | 9/2006 | Eroma et al. |
| 7,198,925 B2 | 4/2007 | Foody |
| 7,218,975 B2 | 5/2007 | Stevens et al. |
| 7,930,085 B2 | 6/2008 | Ishii et al. |
| 7,503,981 B2 | 3/2009 | Wyman et al. |
| 7,807,419 B2 | 10/2010 | Hennessey et al. |
| 7,909,895 B2 | 3/2011 | Dickinson et al. |
| 7,932,063 B2 | 4/2011 | Dunson, Jr. et al. |
| 7,932,065 B2 | 4/2011 | Medoff |
| 7,935,840 B2 | 5/2011 | Leveson et al. |
| 8,003,352 B2 | 8/2011 | Foody et al. |
| 8,024,074 B2 | 9/2011 | Stelford et al. |
| 8,086,354 B2 | 12/2011 | Bondar et al. |
| 8,103,385 B2 | 1/2012 | Macharia et al. |
| 8,110,383 B2 | 2/2012 | Jonsson et al. |
| 8,123,864 B2 | 2/2012 | Christensen et al. |
| 8,168,840 B2 | 5/2012 | Brady et al. |
| 8,318,453 B2 * | 11/2012 | Medoff ............... 435/41 |
| 8,323,923 B1 | 12/2012 | Horton |
| 8,328,947 B2 | 12/2012 | Anand et al. |
| 8,394,277 B2 | 3/2013 | Bonanni et al. |
| 8,426,161 B1 | 4/2013 | Horton |
| 8,529,765 B2 | 9/2013 | Horton |
| 8,563,277 B1 | 10/2013 | Parekh et al. |
| 8,765,430 B2 | 7/2014 | Parekh et al. |
| 2002/0038058 A1 | 3/2002 | Holtzapple et al. |
| 2002/0164730 A1 | 11/2002 | Ballesteros Perdices et al. |
| 2002/0164731 A1 | 11/2002 | Eroma et al. |
| 2002/0192774 A1 | 12/2002 | Ahring et al. |
| 2002/0197686 A1 | 12/2002 | Lightner |
| 2003/0109011 A1 | 6/2003 | Hood et al. |
| 2003/0199049 A1 | 10/2003 | Nguyen et al. |
| 2003/0221361 A1 | 12/2003 | Russell et al. |
| 2003/0224088 A1 | 12/2003 | Burdick |
| 2004/0152881 A1 | 8/2004 | Holtzapple et al. |
| 2004/0168960 A1 | 9/2004 | Holtzapple et al. |
| 2004/0171136 A1 | 9/2004 | Holtzapple et al. |
| 2005/0054064 A1 | 3/2005 | Talluri et al. |
| 2005/0244934 A1 | 11/2005 | Foody et al. |
| 2005/0272134 A1 | 12/2005 | Hughes |
| 2006/0003064 A1 | 1/2006 | James |
| 2006/0024801 A1 | 2/2006 | Holtzapple et al. |
| 2006/0032113 A1 | 2/2006 | Whitney |
| 2006/0069244 A1 | 3/2006 | Holtzapple et al. |
| 2006/0090749 A1 | 5/2006 | Rein et al. |
| 2006/0188980 A1 | 8/2006 | Holtzapple et al. |
| 2006/0211101 A1 | 9/2006 | Chotani et al. |
| 2006/0251764 A1 | 11/2006 | Abbas et al. |
| 2006/0281157 A1 | 12/2006 | Chotani et al. |
| 2007/0037259 A1 | 2/2007 | Hennessey et al. |
| 2007/0118916 A1 | 5/2007 | Puzio et al. |
| 2007/0148750 A1 | 6/2007 | Hoshino et al. |
| 2007/0190626 A1 | 8/2007 | Wilkening et al. |
| 2007/0275447 A1 | 11/2007 | Lewis et al. |
| 2008/0014617 A1 | 1/2008 | Cerea |
| 2008/0057555 A1 | 3/2008 | Nguyen |
| 2008/0121359 A1 | 5/2008 | Holtzapple et al. |
| 2008/0176301 A1 | 7/2008 | Granda et al. |
| 2008/0227162 A1 | 9/2008 | Varanasi et al. |
| 2008/0280338 A1 | 11/2008 | Hall et al. |
| 2008/0286193 A1 | 11/2008 | Bento et al. |
| 2009/0023187 A1 | 1/2009 | Foody et al. |
| 2009/0042259 A1 | 2/2009 | Dale et al. |
| 2009/0043686 A1 | 2/2009 | Matsumoto |
| 2009/0064566 A1 | 3/2009 | Brummerstedt Iversen et al. |
| 2009/0098617 A1 | 4/2009 | Burke et al. |
| 2009/0117635 A1 | 5/2009 | Bradley et al. |
| 2009/0181434 A1 | 7/2009 | Aikens et al. |
| 2009/0298149 A1 | 12/2009 | Wang et al. |
| 2010/0021980 A1 | 1/2010 | McDonald et al. |
| 2010/0041119 A1 | 2/2010 | Christensen et al. |
| 2010/0055741 A1 | 3/2010 | Galvez, II et al. |
| 2010/0143974 A1 | 6/2010 | Chung et al. |
| 2010/0221805 A1 | 9/2010 | Kelly |
| 2010/0221819 A1 | 9/2010 | Foody et al. |
| 2010/0227369 A1 | 9/2010 | Narendranath et al. |
| 2010/0317053 A1 | 12/2010 | Stromberg et al. |
| 2011/0020874 A1 | 1/2011 | Hata |
| 2011/0079219 A1 | 4/2011 | McDonald et al. |
| 2011/0081689 A1 | 4/2011 | Flanegan et al. |
| 2011/0114765 A1 | 5/2011 | Brady et al. |
| 2011/0129886 A1 | 6/2011 | Howard et al. |
| 2011/0201084 A1 | 8/2011 | Wyman et al. |
| 2011/0223641 A1 | 9/2011 | Stephanopoulos et al. |
| 2011/0244499 A1 | 10/2011 | Realff |
| 2011/0258911 A1 | 10/2011 | Hanson et al. |
| 2011/0258913 A1 | 10/2011 | Stamires et al. |
| 2011/0275860 A1 | 11/2011 | Beldring et al. |
| 2011/0300586 A1 | 12/2011 | Liu et al. |
| 2012/0006320 A1 | 1/2012 | Nguyen |
| 2012/0037325 A1 | 2/2012 | Beldring et al. |
| 2012/0041186 A1 | 2/2012 | Pschorn et al. |
| 2012/0100045 A1 | 4/2012 | Beldring et al. |
| 2012/0100577 A1 | 4/2012 | Medoff et al. |
| 2012/0122162 A1 | 5/2012 | Romero et al. |
| 2012/0190092 A1 | 7/2012 | Jaquess et al. |
| 2012/0196233 A1 | 8/2012 | Ni et al. |
| 2012/0211427 A1 | 8/2012 | Bonanni et al. |
| 2012/0214216 A1 | 8/2012 | Brady et al. |
| 2013/0210101 A1 | 8/2013 | Parekh et al. |
| 2013/0274455 A1 | 10/2013 | Parekh et al. |
| 2013/0274456 A1 | 10/2013 | Parekh et al. |
| 2013/0323830 A1 | 12/2013 | Horton |
| 2014/0106418 A1 | 4/2014 | Parekh et al. |
| 2014/0178944 A1 | 6/2014 | Parekh et al. |
| 2014/0188543 A1 | 7/2014 | Pearlmutter et al. |

FOREIGN PATENT DOCUMENTS

| | | |
|---|---|---|
| JP | 2006-149343 A | 6/2006 |
| WO | WO 01/32715 A1 | 5/2001 |
| WO | WO 01/60752 A1 | 8/2001 |
| WO | WO 02/00324 A1 | 1/2002 |
| WO | WO 02/01220 A2 | 1/2002 |
| WO | WO 02/001220 A3 | 9/2002 |
| WO | WO 2004/081193 A2 | 9/2004 |
| WO | WO 2004/108969 A1 | 12/2004 |
| WO | WO 2004/113551 A1 | 12/2004 |
| WO | WO 2005/087937 A2 | 9/2005 |
| WO | WO 2005/118828 A1 | 12/2005 |
| WO | WO 2006/024242 A1 | 3/2006 |
| WO | WO 2006/101832 A2 | 9/2006 |
| WO | WO 2007/009463 A2 | 1/2007 |
| WO | WO 2007/009463 A3 | 7/2007 |
| WO | WO 2008/020901 A2 | 2/2008 |
| WO | WO 2006/101832 A3 | 4/2009 |
| WO | WO 2009/063138 A2 | 5/2009 |
| WO | WO 2009/087680 A2 | 7/2009 |
| WO | WO 2010/056940 A2 | 5/2010 |
| WO | WO 2010/115488 A1 | 10/2010 |
| WO | WO 2010/123932 A1 | 10/2010 |
| WO | WO 2011/003962 A2 | 1/2011 |
| WO | WO 2011/022811 A1 | 3/2011 |
| WO | WO 2011/028853 A1 | 3/2011 |
| WO | WO 2011/103033 A1 | 8/2011 |

(56) References Cited

FOREIGN PATENT DOCUMENTS

| | | |
|---|---|---|
| WO | WO 2012/051523 A1 | 4/2012 |
| WO | WO 2012/099967 A1 | 7/2012 |

OTHER PUBLICATIONS

Ballesteros et al. 2004. Ethanol from lignocellulose materials by a simultaneous saccharification and fermentation process (SFS) with Kluyveromyces marxianus CECT 10875. Process Biochemistry, vol. 39, pp. 1843-1848.*
Aldrich. 2003-2004. Particle size conversion Table, 2 Pages or Page T848 of the Aldrich 2003-2004 Catalog/ Handbook of Fine Chemicals.*
U.S. Appl. No. 13/793,860, filed Mar. 11, 2013, Horton.
Alcohol and Tobacco Tax and Trade Bureau, treasury. 27 C.F.R. §19.134 Bonded warehouse not on premises qualified for production of spirits, p. 381, Apr. 1, 1997 revision.
Boggan. 2003. Alcohol Chemistry and You Sources and Uses of Ethyl Alcohol. Kennesaw State University, pp. 1-5, Printed May 17, 2010. http://www.chemcases.com/alcohol/alc-03.htm/.
Dale, et al. Hydrolysis of lignocellulosics at low enzyme levels: Applications of thr AFEX process. Bioresource Technology. Apr. 1996; 56(1):111-116.
Dasari, et al. The effect of particle size on hydrolysis reaction rates and rheological properties in cellulosic slurries. Appl Biochem Biotechnol. Apr. 2007;136-140(1-12):289-99. doi: 10.1007/s12010-007-9059-x.
Dowe, et al (SSF Experimental Protocols—Ligonocellulosic Biomass Hydrolysis and Fermentation. Laboratory Analytical Procedure (LAP), Issue Date: Oct. 30, 2001. National Renewable Energy Laboratory, 1617 Cole Boulevard, Golden, Colorado 8041-3393. 76 Pages).
Dow, et al. 2001. SSF Experimental Protocols—Lignocellulosic Biomass Hydrolysis and Fermentation Laboratory Analytical Procedure (LAP), National Renewable Energy Laboratory. 1617 Cole Boulevard, Golden, Colorado. Issue Date: Oct. 30, 2001, pp. 1-18.
Gibreel, et al. Fermentation of barley by using *Saccharomyces cerevisiae*: examination of barley as feedstock for bioethanol production value-added products. Appl Environ Microbiol. Mar. 2009;75(5):1363-72. doi: 10.1128/AEM.01512-08. Epub Dec. 29, 2008.
Gum, et al. Structural characterization of a glycoprotein cellulase, 1,4-beta-D-glucan cellubiohydrolase C from trichodermaciride. Biochem. Biophys. Acta. 1976; 446:370-86.
International search report and written opinion dated Jan. 26, 2010 for PCT/US2009/67221.
Jones, et al. (1994, Ethanolic Fermentation of Blackstrap Molasses and Sugarcane Juice Using Very High Gravity Technology. J. Agric. Food Chem, vol. 42, pp. 1242-1246).
Kim, et al. Lime pretreatment and enzymatic hydrolysis of corn stover. Bioresour Technol. Dec. 2005; 96(18):1994-2006.
Kim, et al. Pretreatment and fractionation of corn stover by ammonia recycle percolation process. Bioresour Technol. Dec. 2005;96(18):2007-13.
Lloyd, et al. Combined sugar yields for dilute sulfuric acid pretreatment of corn stover followed by enzymatic hydrolysis of the remaining solids. Bioresour Technol. Dec. 2005;96(18):1967-77.
Mosier, et al. Features of promising technologies for pretreatment of lignoceullulosic biomass. Bioresour Technol. Apr. 2005;96(6):673-86.
Mosier, et al. Optimization of pH controlled liquid hot water pretreatment of corn stover. Bioresour Technol. Dec. 2005;96(18):1986-93.
Nevoigt, et al. Osmoregulation and glycerol metabolism in the yeast *Saccharaomyces cerevisiae*. FEMS Microbiol Rev. Nov. 1997;21(3):231-41.
Notice of allowance dated Oct. 15, 2012 for U.S. Appl. No. 11/974,129.
Office action dated Feb. 20, 2013 for U.S. Appl. No. 13/686,477.
Office action dated Mar. 20, 2013 for U.S. Appl. No. 12/633,555.
Office action dated May 24, 2010 for U.S. Appl. No. 11/974,129.
Office action dated Jul. 6, 2012 for U.S. Appl. No. 11/974,129.
Office action dated Oct. 3, 2012 for U.S. Appl. No. 12/633,555.
Office action dated Nov. 8, 2010 for U.S. Appl. No. 11/974,129.
Parekh, et al. Production of glycerol by hansenula anomala. Biotechnol Bioeng. Jul. 1985;27(7):1089-91.
Santoro, et al. A High-throughput Platform for Screening Milligram Quantities of Plant Biomass for Lignocellulose Digestibility. Bioenerg. Res. Jan. 2010; 3:93-102.
Shapouri et al. 2006. The Economic Feasibility of Ethanol Production from Sugar in The United States, USDA, 78 Pages, Jul. 2006.
Slutter, et al. Determination of structural carbohydrates and lignin in biomass. National Renewable Energy Laboratory. Technical report NREL/TP-510-42618. Revised Jun. 2010.
Taylor. From Raw Sugar to Raw materials. Chemical innovation. 2000; 30:45-48.
USDA, "The Economic Feasibility of Ethanol Production From Sugar in the United States"; Jul. 2006, 69 pages.
Varhegyi, et al. 1989. Kinetics of the thermal decomposistion of cellulose, hemicellulose, and sugarcane bagasse. Energy Fuels, vol. 3, No. 3, pp. 329-335.
Waiss, et al. Improving Digestibility of Straws for Ruminant Feed by Aqueous Ammonia. Journal of Animal Science. 1972; 35(1):109-112.
Waltermann, et al. Rhodoccus opacus strain PD630 as a new source of high-value single-cell oil? Isolation and characterization of triacylglycerols and other storage lipids. Microbiology. 2000; 1143-1149.
U.S. Appl. No. 14/254,441, filed Apr. 16, 2014, Parekh et al.
U.S. Appl. No. 14/340,179, Parekh et al.
Agbor, et al. Biomass pretreatment: fundamentals toward application. Biotechnol Adv. Nov.-Dec. 2011;29(6):675-85. doi: 10.1016/j.biotechnadv.2011.05.005. Epub May 23, 2011.
Brigham, et al. Bacterial Carbon Storage to Value Added Products. J Microbial Biochem Technol 2011, S3-002.
Felix et al. In vitro and in vivo digestibility of soya-bean straw treated with various alkalis. Anim Prod. 1990; 51:47-61.
International search report and written opinion dated May 30, 2013 for PCT/US2013/025457.
International search report and written opinion dated Jun. 20, 2013 for PCT/US2013/036497.
International search report and written opinion dated Jul. 26, 2013 for PCT Application No. US2013/032955.
International search report and written opinion dated Nov. 19, 2013 for PCT/US2013/054411.
International search report dated Aug. 25, 2014 for PCT Application No. US2014/027850.
International search report dated Sep. 8, 2014 for PCT Application No. US2014/039399.
Larsson, et al. Comparison of different methods for the detoxification of lignocellulose hydrolyzates of spruce. Applied Biochemistry and Biotechnology, 1999; 77-79:91-103.
Notice of allowance dated Jan. 9, 2013 for U.S. Appl. No. 13/645,425.
Notice of allowance dated Feb. 20, 2014 for U.S. Appl. No. 13/731,633.
Notice of allowance dated Jun. 7, 2013 for U.S. Appl. No. 12/633,555.
Notice of allowance dated Jul. 8, 2013 for U.S. Appl. No. 13/686,477.
Notice of allowance dated Aug. 8, 2013 for U.S. Appl. No. 12/633,555.
Office action dated Mar. 24, 2014 for U.S. Appl. No. 13/724,763.
Office action dated Jun. 25, 2013 for U.S. Appl. No. 13/731,633.
Office action dated Oct. 18, 2013 for U.S. Appl. No. 13/724,763.
Palmqvist, et al. Fermentation of lignocellulosic hydrolysales I: inhibition and detoxification. Bioresource Technology, 2000; 74(1):17-24.
Office action dated Oct. 8, 2014 for U.S. Appl. No. 13/793,860.
Malherbe, et al. Lignocellulose biodegradation: Fundamentals and applications. Re/Views in Environmental Science & Bio/Technology. 2001; 1:105-114.
Sun, et al. Dilute acid pretreatment of rye straw and bermuda grass for ethanol production. Bioresour Technol. Sep. 2005;96(14):1599-606. Epub Feb. 24, 2005.

* cited by examiner

Paper and Pulp Mills

INTEGRATED WOOD PROCESSING AND SUGAR PRODUCTION

CROSS-REFERENCE

This application is a continuation-in-part application of Ser. No. 13/793,860, filed Mar. 11, 2013; which is a continuation of Ser. No. 13/646,425, filed Oct. 5, 2012, now U.S. Pat. No. 8,426,161; which is a continuation of Ser. No. 11/974,129, filed Oct. 11, 2007, now U.S. Pat. No. 8,323,923; which claimed the benefit of U.S. Provisional Application No. 60/851,424, filed Oct. 13, 2006; this application also claims the benefit of U.S. Provisional Application No. 61/711,588, filed Oct. 9, 2012, each of which application is incorporated herein by reference in its entirety.

BACKGROUND OF THE INVENTION

Processing of woody plants requires optimized pretreatment to extract and hydrolyze cellulosic and hemicellulosic material into sugars and then into other products, such as biofuels and other industrially-valuable chemicals. Just the cost of transporting woody wastes from lumber mills and wood harvesting areas to biofuel or chemical plants contributes to the cost of producing cellulosic sugars, thus reducing the value of any end products. However, constructing costly plants to pretreat and convert woody residues into products such as ethanol, butanol, or succinic acid is time consuming and risky as the mills must consistently produce large amounts of biomass and residues must be sometimes be conveyed from remote sites. With thousands of wood processing mills throughout North America, it would be advantageous to have a system whereby woody biomass can be processed inexpensively at mill sites.

The invention relates generally to a method and system for producing ethanol and more particularly to a method and system for producing ethanol using one or more feedstock processing plants located near a feedstock producing or a feedstock storage site and an ethanol producing plant.

SUMMARY OF THE INVENTION

Disclosed herein are methods for producing sugar from woody feedstock, the methods comprising: (a) providing a woody feedstock comprising cellulose, hemicellulose, and/or lignocellulose; (b) processing the cellulose, hemicellulose, and/or lignocellulose of the woody feedstock at one or more portable feedstock processing units, each of which is located at or near a woody feedstock provider, to produce sugar in a solution; wherein processing comprises mechanical destruction, chemical hydrolysis, and/or enzymatic hydrolysis; (c) transporting the sugar to a plant for processing the sugar into biofuels or chemicals. Some embodiments further comprise: (d) concentrating the sugar in the solution prior to transporting. In some embodiments, the sugar comprises C5 sugars, C6 sugars, or a combination thereof.

In some embodiments, the woody feedstock provider is a timber harvesting site or a mill. In some embodiments, the woody feedstock comprises wood chips, slash, wood, bark, sawdust, paper, poplars, willows, pulp, waste, or a combination thereof. In some embodiments, the processing is performed at a plurality of portable feedstock processing units. In some embodiments, the plant is centrally located relative to the plurality of portable feedstock processing units.

In some embodiments, processing comprises mechanical destruction, chemical hydrolysis, and enzymatic hydrolysis.

In some embodiments, processing comprising mechanical destruction, chemical hydrolysis, and enzymatic hydrolysis comprises: (i) reducing the size of the woody feedstock to uniform 0.2 mm or smaller pieces; (ii) adding water to the woody feedstock to produce a slurry of 10-30% w/v solids; (iii) treating the slurry for no more than 20 minutes at 120-180° C. to produce a first liquid fraction containing C5 sugars and a first solid fraction; (iv) removing and concentrating the first liquid fraction; (v) hydrolyzing the first liquid fraction with at least one hemicellulase enzyme; (vi) treating the first solid fraction at a temperature greater than 190° C. for greater than 5 minutes in a 1-3% acid solution to produce a mixture; (vii) neutralizing the mixture; (viii) hydrolyzing the mixture with cellulase enzymes to produce a second liquid fraction containing C6 sugars and a second solid fraction; and (ix) separating the second liquid fraction from the second solid fraction.

Also disclosed herein are systems for producing sugars, the systems comprising: (a) a woody feedstock provider, the woody feedstock provider being adapted to provide woody feedstock; (b) a woody feedstock comprising cellulose, hemicellulose, and/or lignocellulose; (c) a portable feedstock processing unit that processes the cellulose, hemicellulose, and/or lignocellulose of the woody feedstock to produce sugar in a solution, wherein processing comprises mechanical destruction, chemical hydrolysis, and/or enzymatic hydrolysis; (d) a means for transporting the sugar to a plant for processing the sugar into biofuels or chemicals. In some embodiments, the portable feedstock processing unit is adapted to concentrate the sugar in the solution. In some embodiments, the sugar comprises C5 sugars, C6 sugars, or a combination thereof.

In some embodiments, the portable feedstock processing unit is located at or near the feedstock provider. In some embodiments, the feedstock provider is a timber harvesting site or a mill. In some embodiments, the woody feedstock comprises wood chips, slash, sawdust, paper, pulp, bark, cardboard, other woody residue, or a combination thereof.

In some embodiments, the plant is located near the feedstock provider. Some embodiments comprise a plurality of portable feedstock processing units, each of which is located at or near a feedstock provider. In some embodiments, the plant is centrally located relative to the plurality of portable feedstock processing units.

In some embodiments, processing comprising mechanical destruction, chemical hydrolysis, and/or enzymatic hydrolysis comprises: (i) reducing the size of the woody feedstock to uniform 0.2 mm or smaller pieces; (ii) adding water to the woody feedstock to produce a slurry of 10-30% w/v solids; (iii) treating the slurry for no more than 20 minutes at 120-180° C. to produce a first liquid fraction containing C5 sugars and a first solid fraction; (iv) removing and concentrating the first liquid fraction; (v) hydrolyzing the first liquid fraction with at least one hemicellulase enzymes; (vi) treating the first solid fraction with a temperature greater than 190° C. for greater than 5 minutes in a 1-3% acid solution to produce a mixture; (vii) neutralizing the mixture; (viii) hydrolyzing the mixture with cellulase enzymes to produce a second liquid fraction containing C6 sugars and a second solid fraction; and (ix) separating the second liquid fraction from the second solid fraction. In some embodiments, the woody feedstock comprises wood chips, slash, wood, bark, sawdust, paper, poplars, willows, pulp, waste, or a combination thereof.

Also provided are methods for producing sugar from woody biomass at a mill, the methods comprising the steps of a) providing a woody biomass; b) processing the woody biomass at one or more portable biomass processing units located at or near a woody biomass providing site to produce sugar, wherein processing comprises mechanical destruction, chemical hydrolysis, and/or enzymatic hydrolysis; c) transporting the sugar from the portable biomass processing units to a plant for processing sugar into biofuels or chemicals.

Also provided are systems for producing sugars, the systems comprising: a) a woody feedstock provider, the woody feedstock provider being adapted to provide woody feedstock; b) woody feedstock; c) a portable feedstock processing unit, the portable feedstock processing unit being adapted to produce sugar from the woody biomass at a timber harvesting site or at a mill; d) a means for transporting the sugar.

In some embodiments, the feedstock processing unit is located at or near the feedstock provider. In some embodiments, the feedstock processing unit is adapted to concentrate the sugar. In some embodiments, the feedstock processing unit or biomass processing unit is able to extract sugar from wood chips, slash, sawdust, paper, pulp, bark, cardboard, other woody residue, or a combination thereof. Some embodiments comprise a plurality of portable feedstock processing plants. Some embodiments further comprise a biofuel or chemical producing plant at the mill. Some embodiments further comprise a biofuel or chemical producing plant that is centrally located relative to the mill. In some embodiments, the feedstock comprises cellulose, hemicellulose, and/or lignocellulose biomass. In some embodiments, the feedstock comprises wood chips, slash, sawdust, paper pulp, waste materials, bark, paper, cardboard, or a combination thereof. In some embodiments, the pretreatment comprises dilute-acid thermochemical treatment comprising: a) reducing the size of the biomass to uniform 0.2 mm or smaller pieces; b) adding water to the biomass to produce a slurry of 10-30% w/v solids; c) treating the 10-30% biomass (w/v) with water for no more than 20 minutes at 120-180° C. to produce a first liquid fraction containing C5 sugars and a first solid fraction; d) removing and concentrating the first liquid fraction; e) hydrolyzing the first liquid fraction with at least one hemicellulase enzymes; f) treating the first solid fraction with a temperature greater than 190° C. for greater than 5 minutes in a 1-3% acid solution to produce a mixture; g) neutralizing the mixture; h) hydrolyzing the mixture with cellulase enzymes to produce a second liquid fraction and a second solid fraction; and i) separating the second liquid fraction from the second solid fraction. In some embodiments, the biomass comprises wood chips, slash, wood, bark, sawdust, paper, poplars, willows, pulp, waste, or a combination thereof.

Also disclosed are methods for producing ethanol comprising the steps of providing feedstock, processing the feedstock at a feedstock processing plant adapted to produce sugar water and wet animal feed, separating the sugar water and wet animal feed, transporting the sugar water from the feedstock processing plant to an ethanol producing plant, and producing ethanol from the sugar water. In the preferred embodiments of the method for producing ethanol, the method further comprises the steps of pretreating the feedstock, concentrating, fermenting, distilling, dehydrating and denaturing the sugar water, and selling the ethanol. Also in the preferred embodiments of the invention, the feedstock is processed at or near a feedstock providing site.

Also disclosed are systems for producing ethanol. The preferred system for producing ethanol comprises a feedstock provider adapted to provide feedstock, feedstock, a feedstock processing plant adapted to produce sugar water and wet animal feed from the feedstock, a means for transporting the sugar water, and an ethanol producing plant adapted to produce ethanol from the sugar water. In the preferred embodiments of the system for producing ethanol, the feedstock processing plant is located at or near the feedstock provider and produces a non-hazardous, non-fermented, and non-distilled materials. Also in the preferred embodiments of the system for producing ethanol, the ethanol producing plant is centrally located relative to a plurality of portable feedstock processing plants.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

DETAILED DESCRIPTION OF THE INVENTION

Figure 1:
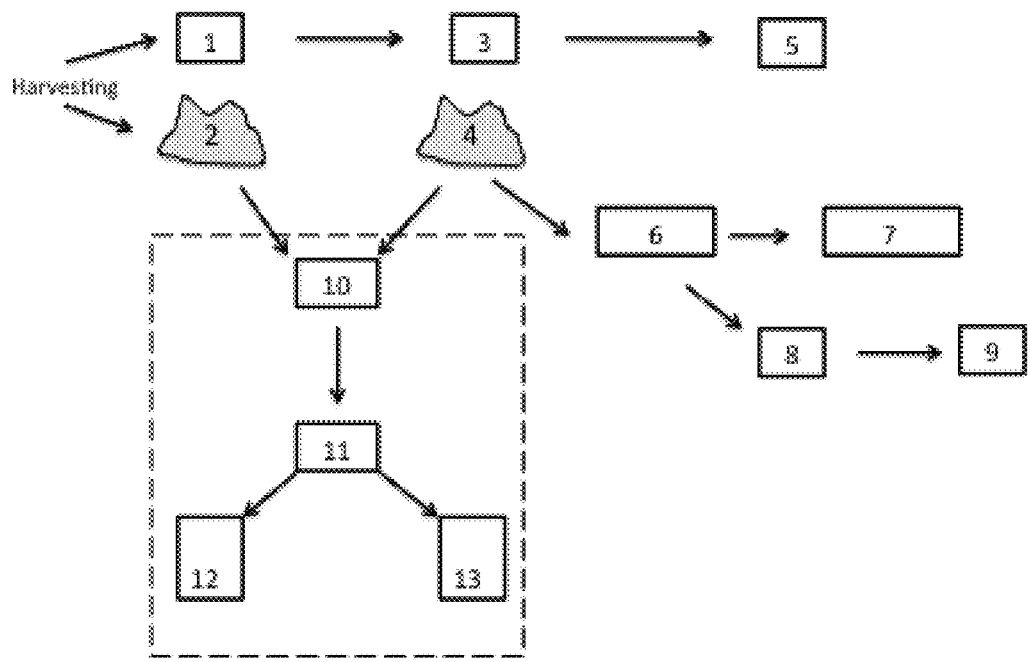
FIG. 1 is a diagram depicting a system for producing sugar hydrolysate products from wood residues at a paper and pulp mill.

As used in the specification and the appended claims, the singular forms "a," "an" and "the" include plural referents unless the context clearly dictates otherwise. Thus, for example, reference to "a purified monomer" includes mixtures of two or more purified monomers. The term "comprising" as used herein is synonymous with "including," "containing," or "characterized by," and is inclusive or open-ended and does not exclude additional, unrecited elements or method steps.

"About" means a referenced numeric indication plus or minus 10% of that referenced numeric indication. For example, the term about 4 would include a range of 3.6 to 4.4. All numbers expressing quantities of ingredients, reaction conditions, and so forth used in the specification are to be understood as being modified in all instances by the term "about." Accordingly, unless indicated to the contrary, the numerical parameters set forth herein are approximations that can vary depending upon the desired properties sought to be obtained. At the very least, and not as an attempt to limit the application of the doctrine of equivalents to the scope of any claims in any application claiming priority to the present application, each numerical parameter should be construed in light of the number of significant digits and ordinary rounding approaches.

Wherever the phrase "for example," "such as," "including" and the like are used herein, the phrase "and without limitation" is understood to follow unless explicitly stated otherwise. Therefore, "for example ethanol production" means "for example and without limitation ethanol production."

In this specification and in the claims that follow, reference will be made to a number of terms which shall be defined to have the following meanings.

Definitions

"Optional" or "optionally" means that the subsequently described event or circumstance may or may not occur, and that the description includes instances where said event or circumstance occurs and instances where it does not. For example, the phrase "the medium can optionally contain glucose" means that the medium may or may not contain glucose as an ingredient and that the description includes both media containing glucose and media not containing glucose.

Unless characterized otherwise, technical and scientific terms used herein have the same meaning as commonly understood by one of ordinary skill in the art.

"Fermentive end-product" and "fermentation end-product" and "end product" are used interchangeably herein to include biofuels, chemicals, compounds suitable as liquid fuels, gaseous fuels, triacylglycerols, reagents, chemical feedstocks, chemical additives, processing aids, food additives, bioplastiks and precursors to bioplastiks, and other products. Examples of fermentive end-products include but are not limited to 1,4 diacids (succinic, fumaric and malic), 2,5 furan dicarboxylic acid, 3 hydroxy propionic acid, aspartic acid, glucaric acid, glutamic acid, itaconic acid, levulinic acid, 3-hydroxybutyrolactone, glycerol, sorbitol, xylitol/arabinitol, butanediol, butanol, methane, methanol, ethane, ethene, ethanol, n-propane, 1-propene, 1-propanol, propanal, acetone, propionate, n-butane, 1-butene, 1-butanol, butanal, butanoate, isobutanal, isobutanol, 2-methylbutanal, 2-methylbutanol, 3-methylbutanal, 3-methylbutanol, 2-butene, 2-butanol, 2-butanone, 2,3-butanediol, 3-hydroxy-2-butanone, 2,3-butanedione, ethylbenzene, ethenylbenzene, 2-phenylethanol, phenylacetaldehyde, 1-phenylbutane, 4-phenyl-1-butene, 4-phenyl-2-butene, 1-phenyl-2-butene, 1-phenyl-2-butanol, 4-phenyl-2-butanol, 1-phenyl-2-butanone, 4-phenyl-2-butanone, 1-phenyl-2,3-butandiol, 1-phenyl-3-hydroxy-2-butanone, 4-phenyl-3-hydroxy-2-butanone, 1-phenyl-2,3-butanedione, n-pentane, ethylphenol, ethenylphenol, 2-(4-hydroxyphenyl)ethanol, 4-hydroxyphenylacetaldehyde, 1-(4-hydroxyphenyl) butane, 4-(4-hydroxyphenyl)-1-butene, 4-(4-hydroxyphenyl)-2-butene, 1-(4-hydroxyphenyl)-1-butene, 1-(4-hydroxyphenyl)-2-butanol, 4-(4-hydroxyphenyl)-2-butanol, 1-(4-hydroxyphenyl)-2-butanone, 4-(4-hydroxyphenyl)-2-butanone, 1-(4-hydroxyphenyl)-2,3-butandiol, 1-(4-hydroxyphenyl)-3-hydroxy-2-butanone, 4-(4-hydroxyphenyl)-3-hydroxy-2-butanone, 1-(4-hydroxyphenyl)-2,3-butanonedione, indolylethane, indolylethene, 2-(indole-3-)ethanol, n-pentane, 1-pentene, 1-pentanol, pentanal, pentanoate, 2-pentene, 2-pentanol, 3-pentanol, 2-pentanone, 3-pentanone, 4-methylpentanal, 4-methylpentanol, 2,3-pentanediol, 2-hydroxy-3-pentanone, 3-hydroxy-2-pentanone, 2,3-pentanedione, 2-methylpentane, 4-methyl-1-pentene, 4-methyl-2-pentene, 4-methyl-3-pentene, 4-methyl-2-pentanol, 2-methyl-3-pentanol, 4-methyl-2-pentanone, 2-methyl-3-pentanone, 4-methyl-2,3-pentanediol, 4-methyl-2-hydroxy-3-pentanone, 4-methyl-3-hydroxy-2-pentanone, 4-methyl-2,3-pentanedione, 1-phenylpentane, 1-phenyl-1-pentene, 1-phenyl-2-pentene, 1-phenyl-3-pentene, 1-phenyl-2-pentanol, 1-phenyl-3-pentanol, 1-phenyl-2-pentanone, 1-phenyl-3-pentanone, 1-phenyl-2,3-pentanediol, 1-phenyl-2-hydroxy-3-pentanone, 1-phenyl-3-hydroxy-2-pentanone, 1-phenyl-2,3-pentanedione, 4-methyl-1-phenylpentane, 4-methyl-1-phenyl-1-pentene, 4-methyl-1-phenyl-2-pentene, 4-methyl-1-phenyl-3-pentene, 4-methyl-1-phenyl-3-pentanol, 4-methyl-1-phenyl-2-pentanol, 4-methyl-1-phenyl-3-pentanone, 4-methyl-1-phenyl-2-pentanone, 4-methyl-1-phenyl-2,3-pentanediol, 4-methyl-1-phenyl-2,3-pentanedione, 4-methyl-1-phenyl-3-hydroxy-2-pentanone, 4-methyl-1-phenyl-2-hydroxy-3-pentanone, 1-(4-hydroxyphenyl)pentane, 1-(4-hydroxyphenyl)-1-pentene, 1-(4-hydroxyphenyl)-2-pentene, 1-(4-hydroxyphenyl)-3-pentene, 1-(4-hydroxyphenyl)-2-pentanol, 1-(4-hydroxyphenyl)-3-pentanol, 1-(4-hydroxyphenyl)-2-pentanone, 1-(4-hydroxyphenyl)-3-pentanone, 1-(4-hydroxyphenyl)-2,3-pentanediol, 1-(4-hydroxyphenyl)-2-hydroxy-3-pentanone, 1-(4-hydroxyphenyl)-3-hydroxy-2-pentanone, 1-(4-hydroxyphenyl)-2,3-pentanedione, 4-methyl-1-(4-hydroxyphenyl)pentane, 4-methyl-1-(4-hydroxyphenyl)-2-pentene, 4-methyl-1-(4-hydroxyphenyl)-3-pentene, 4-methyl-1-(4-hydroxyphenyl)-1-pentene, 4-methyl-1-(4-hydroxyphenyl)-3-pentano 1,4-methyl-1-(4-hydroxyphenyl)-2-pentano 1,4-methyl-1-(4-hydroxyphenyl)-3-pentanone, 4-methyl-1-(4-hydroxyphenyl)-2-pentanone, 4-methyl-1-(4-hydroxyphenyl)-2,3-pentanediol, 4-methyl-1-(4-hydroxyphenyl)-2,3-pentanedione, 4-methyl-1-(4-hydroxyphenyl)-3-hydroxy-2-pentanone, 4-methyl-1-(4-hydroxyphenyl)-2-hydroxy-3-pentanone, 1-indole-3-pentane, 1-(indole-3)-1-pentene, 1-(indole-3)-2-pentene, 1-(indole-3)-3-pentene, 1-(indole-3)-2-pentanol, 1-(indole-3)-3-pentanol, 1-(indole-3)-2-pentanone, 1-(indole-3)-3-pentanone, 1-(indole-3)-2,3-pentanediol, 1-(indole-3)-2-hydroxy-3-pentanone, 1-(indole-3)-3-hydroxy-2-pentanone, 1-(indole-3)-2,3-pentanedione, 4-methyl-1-(indole-3-)pentane, 4-methyl-1-(indole-3)-2-pentene, 4-methyl-1-(indole-3)-3-pentene, 4-methyl-1-(indole-3)-1-pentene, 4-methyl-2-(indole-3)-3-pentanol, 4-methyl-1-(indole-3)-2-pentanol, 4-methyl-1-(indole-3)-3-pentanone, 4-methyl-1-(indole-3)-2-pentanone, 4-methyl-1-(indole-3)-2,3-pentanediol, 4-methyl-1-(indole-3)-2,3-pentanedione, 4-methyl-1-(indole-3)-3-hydroxy-2-pentanone, 4-methyl-1-(indole-3)-2-hydroxy-3-pentanone, n-hexane, 1-hexene, 1-hexanol, hexanal, hexanoate, 2-hexene, 3-hexene, 2-hexanol, 3-hexanol, 2-hexanone, 3-hexanone, 2,3-hexanediol, 2,3-hexanedione, 3,4-hexanediol, 3,4-hexanedione, 2-hydroxy-3-hexanone, 3-hydroxy-2-hexanone, 3-hydroxy-4-hexanone, 4-hydroxy-3-hexanone, 2-methylhexane, 3-methylhexane, 2-methyl-2-hexene, 2-methyl-3-hexene, 5-methyl-1-hexene, 5-methyl-2-hexene, 4-methyl-1-hexene, 4-methyl-2-hexene, 3-methyl-3-hexene, 3-methyl-2-hexene, 3-methyl-1-hexene, 2-methyl-3-hexanol, 5-methyl-2-hexanol, 5-methyl-3-hexanol, 2-methyl-3-hexanone, 5-methyl-2-hexanone, 5-methyl-3-hexanone, 2-methyl-3,4-hexanediol, 2-methyl-3,4-hexanedione, 5-methyl-2,3-hexanediol, 5-methyl-2,3-hexanedione, 4-methyl-2,3-hexanediol, 4-methyl-2,3-hexanedione, 2-methyl-3-hydroxy-4-hexanone, 2-methyl-4-hydroxy-3-hexanone, 5-methyl-2-hydroxy-3-hexanone, 5-methyl-3-hydroxy-2-hexanone, 4-methyl-2-hydroxy-3-hexanone, 4-methyl-3-hydroxy-2-hexanone, 2,5-dimethylhexane, 2,5-dimethyl-2-hexene, 2,5-dimethyl-3-hexene, 2,5-dimethyl-3-hexanol, 2,5-dimethyl-3-hexanone, 2,5-dimethyl-3,4-hexanediol, 2,5-dimethyl-3,4-hexanedione, 2,5-dimethyl-3-hydroxy-4-hexanone, 5-methyl-1-phenylhexane, 4-methyl-1-phenylhexane, 5-methyl-1-phenyl-1-hexene, 5-methyl-1-phenyl-2-hexene, 5-methyl-1-phenyl-3-hexene, 4-methyl-1-phenyl-1-hexene, 4-methyl-1-phenyl-2-hexene, 4-methyl-1-phenyl-3-hexene, 5-methyl-1-phenyl-2-hexanol, 5-methyl-1-phenyl-3-hexanol, 4-methyl-1-phenyl-2-hexanol, 4-methyl-1-phenyl-3-hexanol, 5-methyl-1-phenyl-2-hexanone, 5-methyl-1-phenyl-3-hexanone, 4-methyl-1-phenyl-2-hexanone, 4-methyl-1-phenyl-3-hexanone, 5-methyl-1-phenyl-2,3-hexanediol, 4-methyl-1-phenyl-2,3-hexanediol, 5-methyl-1-phenyl-3-hydroxy-2-hexanone, 5-methyl-1-phenyl-2-hydroxy-3-hexanone, 4-methyl-1-phenyl-3-hydroxy-2-hexanone, 4-methyl-1-phenyl-2-hydroxy-3-hexanone, 5-methyl-1-phenyl-2,3-hexanedione, 4-methyl-1-phenyl-2,3-hexanedione, 4-methyl-1-(4-hydroxyphenyl)hexane, 5-methyl-1-(4-hydroxyphenyl)-1-hexene, 5-methyl-1-(4-hydroxyphenyl)-2-hexene, 5-methyl-1-(4-hydroxyphenyl)-3-hexene, 4-methyl-1-(4-hydroxyphenyl)-1-hexene, 4-methyl-1-(4-hydroxyphenyl)-2-hexene, 4-methyl-1-(4-hydroxyphenyl)-3-hexene, 5-methyl-1-(4-hydroxyphenyl)-2-hexanol, 5-methyl-1-(4-hydroxyphenyl)-3-hexanol, 4-methyl-1-(4-hydroxyphenyl)-2-hexanol, 4-methyl-1-(4-hydroxyphenyl)-3-hexanol, 5-methyl-1-(4-hydroxyphenyl)-2-hexanone, 5-methyl-1-(4-hydroxyphenyl)-3-hexanone, 4-methyl-1-(4-hydroxyphenyl)-2-hexanone, 4-methyl-1-(4-hydroxyphenyl)-3-hexanone, 5-methyl-1-(4-hydroxyphenyl)-2,3-hexanediol, 4-methyl-1-(4-hydroxyphenyl)-2,3-hexanediol, 5-methyl-1-(4-hydroxyphenyl)-3-hydroxy-2-hexanone, 5-methyl-1-(4-hydroxyphenyl)-2-hydroxy-3-hexanone, 4-methyl-1-(4-hydroxyphenyl)-3-hydroxy-2-hexanone, 4-methyl-1-(4-hydroxyphenyl)-2-hydroxy-3-hexanone, 5-methyl-1-(4-hydroxyphenyl)-2,3-hexanedione, 4-methyl-1-(4-hydroxyphenyl)-2,3-hexanedione, 4-methyl-1-(indole-3-)hexane, 5-methyl-1-(indole-3)-1-hexene, 5-methyl-1-(indole-3)-2-hexene, 5-methyl-1-(indole-3)-3-hexene, 4-methyl-1-(indole-3)-1-hexene, 4-methyl-1-(indole-3)-2-hexene, 4-methyl-1-(indole-3)-3-hexene, 5-methyl-1-(indole-3)-2-hexanol, 5-methyl-1-(indole-3)-3-hexanol, 4-methyl-1-(indole-3)-2-hexanol, 4-methyl-1-(indole-3)-3-hexanol, 5-methyl-1-(indole-3)-2-hexanone, 5-methyl-1-(indole-3)-3-hexanone, 4-methyl-1-(indole-3)-2-hexanone, 4-methyl-1-(indole-3)-3-hexanone, 5-methyl-1-(indole-3)-2,3-hexanediol, 4-methyl-1-(indole-3)-2,3-hexanediol, 5-methyl-1-(indole-3)-3-hydroxy-2-hexanone, 5-methyl-1-(indole-3)-2-hydroxy-3-hexanone, 4-methyl-1-(indole-3)-3-hydroxy-2-hexanone, 4-methyl-1-(indole-3)-2-hydroxy-3-hexanone, 5-methyl-1-(indole-3)-2,3-hexanedione, 4-methyl-1-(indole-3)-2,3-hexanedione, n-heptane, 1-heptene, 1-heptanol, heptanal, heptanoate, 2-heptene, 3-heptene, 2-heptanol, 3-heptanol, 4-heptanol, 2-heptanone, 3-heptanone, 4-heptanone, 2,3-heptanediol, 2,3-heptanedione, 3,4-heptanediol, 3,4-heptanedione, 2-hydroxy-3-heptanone, 3-hydroxy-2-heptanone, 3-hydroxy-4-heptanone, 4-hydroxy-3-heptanone, 2-methylheptane, 3-methylheptane, 6-methyl-2-heptene, 6-methyl-3-heptene, 2-methyl-3-heptene, 2-methyl-2-heptene, 5-methyl-2-heptene, 5-methyl-3-heptene, 3-methyl-3-heptene, 2-methyl-3-heptanol, 2-methyl-4-heptanol, 6-methyl-3-heptanol, 5-methyl-3-heptanol, 3-methyl-4-heptanol, 2-methyl-3-heptanone, 2-methyl-4-heptanone, 6-methyl-3-heptanone, 5-methyl-3-heptanone, 3-methyl-4-heptanone, 2-methyl-3,4-heptanediol, 2-methyl-3,4-heptanedione, 6-methyl-3,4-heptanediol, 6-methyl-3,4-heptanedione, 5-methyl-3,4-heptanediol, 5-methyl-3,4-heptanedione, 2-methyl-3-hydroxy-4-heptanone, 2-methyl-4-hydroxy-3-heptanone, 6-methyl-3-hydroxy-4-heptanone, 6-methyl-4-hydroxy-3-heptanone, 5-methyl-3-hydroxy-4-heptanone, 5-methyl-4-hydroxy-3-heptanone, 2,6-dimethylheptane, 2,5-dimethylheptane, 2,6-dimethyl-2-heptene, 2,6-dimethyl-3-heptene, 2,5-dimethyl-2-heptene, 2,5-dimethyl-3-heptene, 3,6-dimethyl-3-heptene, 2,6-dimethyl-3-heptanol, 2,6-dimethyl-4-heptanol, 2,5-dimethyl-3-heptanol, 2,5-dimethyl-4-heptanol, 2,6-dimethyl-3,4-heptanediol, 2,6-dimethyl-3,4-heptanedione, 2,5-dimethyl-3,4-heptanediol, 2,5-dimethyl-3,4-heptanedione, 2,6-dimethyl-3-hydroxy-4-heptanone, 2,6-dimethyl-4-hydroxy-3-heptanone, 2,5-dimethyl-3-hydroxy-4-heptanone, 2,5-dimethyl-4-hydroxy-3-heptanone, n-octane, 1-octene, 2-octene, 1-octanol, octanal, octanoate, 3-octene, 4-octene, 4-octanol, 4-octanone, 4,5-octanediol, 4,5-octanedione, 4-hydroxy-5-octanone, 2-methyloctane, 2-methyl-3-octene, 2-methyl-4-octene, 7-methyl-3-octene, 3-methyl-3-octene, 3-methyl-4-octene, 6-methyl-3-octene, 2-methyl-4-octanol, 7-methyl-4-octanol, 3-methyl-4-octanol, 6-methyl-4-octanol, 2-methyl-4-octanone, 7-methyl-4-octanone, 3-methyl-4-octanone, 6-methyl-4-octanone, 2-methyl-4,5-octanediol, 2-methyl-4,5-octanedione, 3-methyl-4,5-octanediol, 3-methyl-4,5-octanedione, 2-methyl-4-hydroxy-5-octanone, 2-methyl-5-hydroxy-4-octanone, 3-methyl-4-hydroxy-5-octanone, 3-methyl-5-hydroxy-4-octanone, 2,7-dimethyloctane, 2,7-dimethyl-3-octene, 2,7-dimethyl-4-octene, 2,7-dimethyl-4-octanol, 2,7-dimethyl-4-octanone, 2,7-dimethyl-4,5-octanediol, 2,7-dimethyl-4,5-octanedione, 2,7-dimethyl-4-hydroxy-5-octanone, 2,6-dimethyloctane, 2,6-dimethyl-3-octene, 2,6-dimethyl-4-octene, 3,7-dimethyl-3-octene, 2,6-dimethyl-4-octanol, 3,7-dimethyl-4-octanol, 2,6-dimethyl-4-octanone, 3,7-dimethyl-4-octanone, 2,6-dimethyl-4,5-octanediol, 2,6-dimethyl-4,5-octanedione, 2,6-dimethyl-4-hydroxy-5-octanone, 2,6-dimethyl-5-hydroxy-4-octanone, 3,6-dimethyloctane, 3,6-dimethyl-3-octene, 3,6-dimethyl-4-octene, 3,6-dimethyl-4-octanol, 3,6-dimethyl-4-octanone, 3,6-dimethyl-4,5-octanediol, 3,6-dimethyl-4,5-octanedione, 3,6-dimethyl-4-hydroxy-5-octanone, n-nonane, 1-nonene, 1-nonanol, nonanal, nonanoate, 2-methylnonane, 2-methyl-4-nonene, 2-methyl-5-nonene, 8-methyl-4-nonene, 2-methyl-5-nonanol, 8-methyl-4-nonanol, 2-methyl-5-nonanone, 8-methyl-4-nonanone, 8-methyl-4,5-nonanediol, 8-methyl-4,5-nonanedione, 8-methyl-4-hydroxy-5-nonanone, 8-methyl-5-hydroxy-4-nonanone, 2,8-dimethylnonane, 2,8-dimethyl-3-nonene, 2,8-dimethyl-4-nonene, 2,8-dimethyl-5-nonene, 2,8-dimethyl-4-nonanol, 2,8-dimethyl-5-nonanol, 2,8-dimethyl-4-nonanone, 2,8-dimethyl-5-nonanone, 2,8-dimethyl-4,5-nonanediol, 2,8-dimethyl-4,5-nonanedione, 2,8-dimethyl-4-hydroxy-5-nonanone, 2,8-dimethyl-5-hydroxy-4-nonanone, 2,7-dimethylnonane, 3,8-dimethyl-3-nonene, 3,8-dimethyl-4-nonene, 3,8-dimethyl-5-nonene, 3,8-dimethyl-4-nonanol, 3,8-dimethyl-5-nonanol, 3,8-dimethyl-4-nonanone, 3,8-dimethyl-5-nonanone, 3,8-dimethyl-4,5-nonanediol, 3,8-dimethyl-4,5-nonanedione, 3,8-dimethyl-4-hydroxy-5-nonanone, 3,8-dimethyl-5-hydroxy-4-nonanone, n-decane, 1-decene, 1-decanol, decanoate, 2,9-dimethyldecane, 2,9-dimethyl-3-decene, 2,9-dimethyl-4-decene, 2,9-dimethyl-5-decanol, 2,9-dimethyl-5-decanone, 2,9-dimethyl-5,6-decanediol, 2,9-dimethyl-6-hydroxy-5-decanone, 2,9-dimethyl-5,6-decanedionen-undecane, 1-undecene, 1-undecanol, undecanal, undecanoate, n-dodecane, 1-dodecene, 1-dodecanol, dodecanal, dodecanoate, n-dodecane, 1-decadecene, n-tridecane, 1-tridecene, 1-tridecanol, tridecanal, tridecanoate, n-tetradecane, 1-tetradecene, 1-tetradecanol, tetradecanal, tetradecanoate, n-pentadecane, 1-pentadecene, 1-pentadecanol, pentadecanal, pentadecanoate, n-hexadecane, 1-hexadecene, 1-hexadecanol, hexadecanal, hexadecanoate, n-heptadecane, 1-heptadecene, 1-heptadecanol, heptadecanal, heptadecanoate, n-octadecane, 1-octadecene, 1-octadecanol, octadecanal, octadecanoate, n-nonadecane, 1-nonadecene, 1-nonadecanol, nonadecanal, nonadecanoate, eicosane, 1-eicosene, 1-eicosanol, eicosanal, eicosanoate, 3-hydroxy propanal, 1,3-propanediol, 4-hydroxybutanal, 1,4-butanediol, 3-hydroxy-2-butanone, 2,3-butandiol, 1,5-pentane diol, homocitrate, homoisocitorate, b-hydroxy adipate, glutarate, glutarsemialdehyde, glutaraldehyde, 2-hydroxy-1-cyclopentanone, 1,2-cyclopentanediol, cyclopentanone, cyclopentanol, (S)-2-acetolactate, (R)-2,3-Dihydroxy-isovalerate, 2-oxoisovalerate, isobutyryl-CoA, isobutyrate, isobutyraldehyde, 5-amino pentaldehyde, 1,10-diaminodecane, 1,10-diamino-5-decene, 1,10-diamino-5-hydroxydecane, 1,10-diamino-5-decanone, 1,10-diamino-5,6-decanediol, 1,10-diamino-6-hydroxy-5-decanone, phenylacetoaldehyde, 1,4-diphenylbutane, 1,4-diphenyl-1-butene, 1,4-diphenyl-2-butene, 1,4-diphenyl-2-butanol, 1,4-diphenyl-2-butanone, 1,4-diphenyl-2,3-butanediol, 1,4-diphenyl-3-hydroxy-2-butanone, 1-(4-hydeoxyphenyl)-4-phenylbutane, 1-(4-hydeoxyphenyl)-4-phenyl-1-butene, 1-(4-hydeoxyphenyl)-4-phenyl-2-butene, 1-(4-hydeoxyphenyl)-4-phenyl-2-butanol, 1-(4-hydeoxyphenyl)-4-phenyl-2-butanone, 1-(4-hydeoxyphenyl)-4-phenyl-2,3-butanediol, 1-(4-hydeoxyphenyl)-4-phenyl-3-hydroxy-2-butanone, 1-(indole-3)-4-phenylbutane, 1-(indole-3)-4-phenyl-1-butene, 1-(indole-3)-4-phenyl-2-butene, 1-(indole-3)-4-phenyl-2-butanol, 1-(indole-3)-4-phenyl-2-butanone, 1-(indole-3)-4-phenyl-2,3-butanediol, 1-(indole-3)-4-phenyl-3-hydroxy-2-butanone, 4-hydroxyphenylacetoaldehyde, 1,4-di(4-hydroxyphenyl)butane, 1,4-di(4-hydroxyphenyl)-1-butene, 1,4-di(4-hydroxyphenyl)-2-butene, 1,4-di(4-hydroxyphenyl)-2-butanol, 1,4-di(4-hydroxyphenyl)-2-butanone, 1,4-di(4-hydroxyphenyl)-2,3-butanediol, 1,4-di(4-hydroxyphenyl)-3-hydroxy-2-butanone, 1-(4-hydroxyphenyl)-4-(indole-3-) butane, 1-(4-hydroxyphenyl)-4-(indole-3)-1-butene, 1-di(4-hydroxyphenyl)-4-(indole-3)-2-butene, 1-(4-hydroxyphenyl)-4-(indole-3)-2-butanol, 1-(4-hydroxyphenyl)-4-(indole-3)-2-butanone, 1-(4-hydroxyphenyl)-4-(indole-3)-2,3-butanediol, 1-(4-hydroxyphenyl-4-(indole-3)-3-hydroxy-2-butanone, indole-3-acetoaldehyde, 1,4-di(indole-3-)butane, 1,4-di(indole-3)-1-butene, 1,4-di(indole-3)-2-butene, 1,4-di(indole-3)-2-butanol, 1,4-di(indole-3)-2-butanone, 1,4-di(indole-3)-2,3-butanediol, 1,4-di(indole-3)-3-hydroxy-2-butanone, succinate semialdehyde, hexane-1,8-dicarboxylic acid, 3-hexene-1,8-dicarboxylic acid, 3-hydroxy-hexane-1,8-dicarboxylic acid, 3-hexanone-1,8-dicarboxylic acid, 3,4-hexanediol-1,8-dicarboxylic acid, 4-hydroxy-3-hexanone-1,8-dicarboxylic acid, glycerol, fucoidan, iodine, chlorophyll, carotenoid, calcium, magnesium, iron, sodium, potassium, phosphate, lactic acid, acetic acid, formic acid, isoprenoids, and polyisoprenes, including rubber. Further, such products can include succinic acid, pyruvic acid, enzymes such as cellulases, polysaccharases, lipases, proteases, ligninases, and hemicellulases and may be present as a pure compound, a mixture, or an impure or diluted form.

Fermentation end-products can include polyols or sugar alcohols; for example, methanol, glycol, glycerol, erythritol, threitol, arabitol, xylitol, ribitol, mannitol, sorbitol, dulcitol, fucitol, iditol, inositol, volemitol, isomalt, maltitol, lactitol, and/or polyglycitol.

The term "fatty acid comprising material" as used herein has its ordinary meaning as known to those skilled in the art and can comprise one or more chemical compounds that include one or more fatty acid moieties as well as derivatives of these compounds and materials that comprise one or more of these compounds. Common examples of compounds that include one or more fatty acid moieties include triacylglycerides, diacylglycerides, monoacylglycerides, phospholipids, lysophospholipids, free fatty acids, fatty acid salts, soaps, fatty acid comprising amides, esters of fatty acids and monohydric alcohols, esters of fatty acids and polyhydric alcohols including glycols (e.g. ethylene glycol, propylene glycol, etc.), esters of fatty acids and polyethylene glycol, esters of fatty acids and polyethers, esters of fatty acids and polyglycol, esters of fatty acids and saccharides, esters of fatty acids with other hydroxyl-containing compounds, etc. A fatty acid comprising material can be one or more of these compounds in an isolated or purified form. It can be a material that includes one or more of these compounds that is combined or blended with other similar or different materials. It can be a material where the fatty acid comprising material occurs with or is provided with other similar or different materials, such as vegetable and animal oils; mixtures of vegetable and animal oils; vegetable and animal oil byproducts; mixtures of vegetable and animal oil byproducts; vegetable and animal wax esters; mixtures, derivatives and byproducts of vegetable and animal wax esters; seeds; processed seeds; seed byproducts; nuts; processed nuts; nut byproducts; animal matter; processed animal matter; byproducts of animal matter; corn; processed corn; corn byproducts; distiller's grains; beans; processed beans; bean byproducts; soy products; lipid containing plant, fish or animal matter; processed lipid containing plant or animal matter; byproducts of lipid containing plant, fish or animal matter; lipid containing microbial material; processed lipid containing microbial material; and byproducts of lipid containing microbial matter. Such materials can be utilized in liquid or solid forms. Solid forms include whole forms, such as cells, beans, and seeds; ground, chopped, slurried, extracted, flaked, milled, etc. The fatty acid portion of the fatty acid comprising compound can be a simple fatty acid, such as one that includes a carboxyl group attached to a substituted or un-substituted alkyl group. The substituted or unsubstituted alkyl group can be straight or branched, saturated or unsaturated. Substitutions on the alkyl group can include hydroxyls, phosphates, halogens, alkoxy, or aryl groups. The substituted or unsubstituted alkyl group can have 7 to 29 carbons and preferably 11 to 23 carbons (e.g., 8 to 30 carbons and preferably 12 to 24 carbons counting the carboxyl group) arranged in a linear chain with or without side chains and/or substitutions. Addition of the fatty acid comprising compound can be by way of adding a material comprising the fatty acid comprising compound.

The term "pH modifier" as used herein has its ordinary meaning as known to those skilled in the art and can include any material that will tend to increase, decrease or hold steady the pH of the broth or medium. A pH modifier can be an acid, a base, a buffer, or a material that reacts with other materials present to serve to raise, lower, or hold steady the pH. In one embodiment, more than one pH modifier can be used, such as more than one acid, more than one base, one or more acid with one or more bases, one or more acids with one or more buffers, one or more bases with one or more buffers, or one or more acids with one or more bases with one or more buffers. In one embodiment, a buffer can be produced in the broth or medium or separately and used as an ingredient by at least partially reacting in acid or base with a base or an acid, respectively. When more than one pH modifiers are utilized, they can be added at the same time or at different times. In one embodiment, one or more acids and one or more bases are combined, resulting in a buffer. In one embodiment, media components, such as a carbon source or a nitrogen source serve as a pH modifier; suitable media components include those with high or low pH or those with buffering capacity. Exemplary media components include acid- or base-hydrolyzed plant polysaccharides having residual acid or base, ammonia fiber explosion (AFEX) treated plant material with residual ammonia, lactic acid, corn steep solids or liquor.

"Growth phase" is used herein to describe the type of cellular growth that occurs after the "Initiation phase" and before the "Stationary phase" and the "Death phase." The growth phase is sometimes referred to as the exponential phase or log phase or logarithmic phase.

The term "plant polysaccharide" as used herein has its ordinary meaning as known to those skilled in the art and can comprise one or more polymers of sugars and sugar derivatives as well as derivatives of sugar polymers and/or other polymeric materials that occur in plant matter. Exemplary plant polysaccharides include lignin, cellulose, starch, pectin, and hemicellulose. Others are chitin, sulfonated polysaccharides such as alginic acid, agarose, carrageenan, porphyran, furcelleran and funoran. Generally, the polysaccharide can have two or more sugar units or derivatives of sugar units. The sugar units and/or derivatives of sugar units can repeat in a regular pattern, or otherwise. The sugar units can be hexose units or pentose units, or combinations of these. The derivatives of sugar units can be sugar alcohols, sugar acids, amino sugars, etc. The polysaccharides can be linear, branched, cross-linked, or a mixture thereof. One type or class of polysaccharide can be cross-linked to another type or class of polysaccharide.

The term "saccharification" as used herein has its ordinary meaning as known to those skilled in the art and can include conversion of plant polysaccharides to lower molecular weight species that can be utilized by the organism at hand. For some organisms, this would include conversion to monosaccharides, disaccharides, trisaccharides, and oligosaccharides of up to about seven monomer units, as well as similar sized chains of sugar derivatives and combinations of sugars and sugar derivatives.

The terms "SSF" and "SHF" are known to those skilled in the art; SSF meaning simultaneous saccharification and fermentation, or the conversion from polysaccharides or oligosaccharides into monosaccharides at the same time and in the same fermentation vessel wherein monosaccharides are converted to another chemical product such as ethanol. "SHF" indicates a physical separation of the polymer hydrolysis or saccharification and fermentation processes.

The term "biomass" as used herein has its ordinary meaning as known to those skilled in the art and can include one or more biological materials that can be converted into a biofuel, chemical or other product. Biomass as used herein is synonymous with the term "feedstock" and includes corn syrup, molasses, silage, agricultural residues (corn stalks, grass, straw, grain hulls, bagasse, etc.), animal waste (manure from cattle, poultry, and hogs), Distillers Dried Solubles (DDS), Distillers Dried Grains (DDG), Condensed Distillers Solubles (CDS), Distillers Wet Grains (DWG), Distillers Dried Grains with Solubles (DDGS), woody materials (wood or bark, sawdust, timber slash, wood chips, and mill scrap), municipal waste (waste paper, recycled toilet papers, yard clippings, etc.), and energy crops (poplars, willows, switchgrass, alfalfa, prairie bluestem, algae, including macroalgae, etc.). One exemplary source of biomass is plant matter. Plant matter can be, for example, woody plant matter, non-woody plant matter, cellulosic material, lignocellulosic material, hemicellulosic material, carbohydrates, pectin, starch, inulin, fructans, glucans, corn, sugar cane, grasses, switchgrass, sorghum, high biomass sorghum, bamboo, algae and material derived from these. Plants can be in their natural state or genetically modified, e.g., to increase the cellulosic or hemicellulosic portion of the cell wall, or to produce additional exogenous or endogenous enzymes to increase the separation of cell wall components. Plant matter can be further described by reference to the chemical species present, such as proteins, polysaccharides and oils. Polysaccharides include polymers of various monosaccharides and derivatives of monosaccharides including glucose, fructose, lactose, galacturonic acid, rhamnose, etc. Plant matter also includes agricultural waste byproducts or side streams such as pomace, corn steep liquor, corn steep solids, distillers grains, peels, pits, fermentation waste, straw, lumber, sewage, garbage and food leftovers. Peels can be citrus which include, but are not limited to, tangerine peel, grapefruit peel, orange peel, tangerine peel, lime peel and lemon peel. These materials can come from farms, forestry, industrial sources, households, etc. Another non-limiting example of biomass is animal matter, including, for example milk, meat, fat, animal processing waste, and animal waste. "Feedstock" is frequently used to refer to biomass being used for a process, such as those described herein.

"Broth" is used herein to refer to inoculated medium at any stage of growth, including the point immediately after inoculation and the period after any or all cellular activity has ceased and can include the material after post-fermentation processing. It includes the entire contents of the combination of soluble and insoluble matter, suspended matter, cells and medium, as appropriate.

The term "productivity" as used herein has its ordinary meaning as known to those skilled in the art and can include the mass of a material of interest produced in a given time in a given volume. Units can be, for example, grams per liter-hour, or some other combination of mass, volume, and time. In fermentation, productivity is frequently used to characterize how fast a product can be made within a given fermentation volume. The volume can be referenced to the total volume of the fermentation vessel, the working volume of the fermentation vessel, or the actual volume of broth being fermented. The context of the phrase will indicate the meaning intended to one of skill in the art. Productivity is different from "titer" in that productivity includes a time term, and titer is analogous to concentration. Titer and Productivity can generally be measured at any time during the fermentation, such as at the beginning, the end, or at some intermediate time, with titer relating the amount of a particular material present or produced at the point in time of interest and the productivity relating the amount of a particular material produced per liter in a given amount of time. The amount of time used in the productivity determination can be from the beginning of the fermentation or from some other time, and go to the end of the fermentation, such as when no additional material is produced or when harvest occurs, or some other time as indicated by the context of the use of the term. "Overall productivity" refers to the productivity determined by utilizing the final titer and the overall fermentation time.

"Titer" refers to the amount of a particular material present in a fermentation broth. It is similar to concentration and can refer to the amount of material made by the organism in the broth from all fermentation cycles, or the amount of material made in the current fermentation cycle or over a given period of time, or the amount of material present from whatever source, such as produced by the organism or added to the broth. Frequently, the titer of soluble species will be referenced to the liquid portion of the broth, with insolubles removed, and the titer of insoluble species will be referenced to the total amount of broth with insoluble species being present, however, the titer of soluble species can be referenced to the total broth volume and the titer of insoluble species can be referenced to the liquid portion, with the context indicating the which system is used with both reference systems intended in some cases. Frequently, the value determined referenced to one system will be the same or a sufficient approximation of the value referenced to the other.

"Concentration" when referring to material in the broth or in solution generally refers to the amount of a material present from all sources, whether made by the organism or added to the broth or solution. Concentration can refer to soluble species or insoluble species, and is referenced to either the liquid portion of the broth or the total volume of the broth, as for "titer." When referring to a solution, such as "concentration of the sugar in solution", the term indicates increasing one or more components of the solution through evaporation, filtering, extraction, crystallization, etc., by removal or reduction of a liquid portion.

The term "biocatalyst" as used herein has its ordinary meaning as known to those skilled in the art and can include one or more enzymes and/or microorganisms, including solutions, suspensions, and mixtures of enzymes and microorganisms. In some contexts this word will refer to the possible use of either enzymes or microorganisms to serve a particular function, in other contexts the word will refer to the combined use of the two, and in other contexts the word will refer to only one of the two. The context of the phrase will indicate the meaning intended to one of skill in the art. For example, a biocatalyst can be a fermenting microorganism.

The terms "conversion efficiency" or "yield" as used herein have their ordinary meaning as known to those skilled in the art and can include the mass of product made from a mass of substrate. The term can be expressed as a percentage yield of the product from a starting mass of substrate. For the production of ethanol from glucose, the net reaction is generally accepted as:

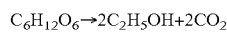

$$C_6H_{12}O_6 \rightarrow 2C_2H_5OH + 2CO_2$$

and the theoretical maximum conversion efficiency, or yield, is 51% (wt.). Frequently, the conversion efficiency will be referenced to the theoretical maximum, for example, "80% of the theoretical maximum." In the case of conversion of glucose to ethanol, this statement would indicate a conversion efficiency of 41% (wt.). The context of the phrase will indicate the substrate and product intended to one of skill in the art.

"Pretreatment" or "pretreated" is used herein to refer to any mechanical, chemical, thermal, biochemical process or combination of these processes whether in a combined step or performed sequentially, that achieves disruption or expansion of the biomass so as to render the biomass more susceptible to attack by enzymes and/or microbes, and can include the enzymatic hydrolysis of released carbohydrate polymers or oligomers to monomers. In one embodiment, pretreatment includes removal or disruption of lignin so as to make the cellulose and hemicellulose polymers in the plant biomass more available to cellulolytic enzymes and/or microbes, for example, by treatment with acid or base. In one embodiment, pretreatment includes disruption or expansion of cellulosic and/or hemicellulosic material. In another embodiment, it can refer to starch release and/or enzymatic hydrolysis to glucose. Steam explosion, and ammonia fiber expansion (or explosion) (AFEX) are well known thermal/chemical techniques. Hydrolysis, including methods that utilize acids, bases, and/or enzymes can be used. Other thermal, chemical, biochemical, enzymatic techniques can also be used.

"Fed-batch" or "fed-batch fermentation" is used herein to include methods of culturing microorganisms where nutrients, other medium components, or biocatalysts (including, for example, enzymes, fresh organisms, extracellular broth, genetically modified plants and/or organisms, etc.) are supplied to the fermentor during cultivation, but culture broth is not harvested from the fermentor until the end of the fermentation, although it can also include "self seeding" or "partial harvest" techniques where a portion of the fermentor volume is harvested and then fresh medium is added to the remaining broth in the fermentor, with at least a portion of the inoculum being the broth that was left in the fermentor. During a fed-batch fermentation, the broth volume can increase, at least for a period, by adding medium or nutrients to the broth while fermentation organisms are present. Suitable nutrients which can be utilized include those that are soluble, insoluble, and partially soluble, including gasses, liquids and solids. In one embodiment, a fed-batch process is referred to with a phrase such as, "fed-batch with cell augmentation." This phrase can include an operation where nutrients and cells are added or one where cells with no substantial amount of nutrients are added. The more general phrase "fed-batch" encompasses these operations as well. The context where any of these phrases is used will indicate to one of skill in the art the techniques being considered.

"Sugar compounds" or "sugar streams" is used herein to indicate mostly monosaccharide sugars, dissolved, crystallized, evaporated, or partially dissolved, including but not limited to hexoses and pentoses; sugar alcohols; sugar acids; sugar amines; compounds containing two or more of these linked together directly or indirectly through covalent or ionic bonds; and mixtures thereof. Included within this description are disaccharides; trisaccharides; oligosaccharides; polysaccharides; and sugar chains, branched and/or linear, of any length. A sugar stream can consist of primarily or substantially C6 sugars, C5 sugars, or mixtures of both C6 and C5 sugars in varying ratios of said sugars. C6 sugars have a six-carbon molecular backbone and C5 sugars have a five-carbon molecular backbone.

"C5-rich" composition means that one or more steps have been taken to remove at least some of the C6 sugars originally in the composition. For example, a C5-rich composition can include no more than about 50% C6 sugars, nor more than about 40% C6 sugars, no more than about 30% C6 sugars, no more than about 20% C6 sugars, no more than about 10% C6 sugars, no more than about 5% C6 sugars, or it can include from about 2% to about 10% C6 sugars by weight. Likewise, a "C6-rich" composition is one in which at least some of the originally-present C5 sugars have been removed. For example, a C6-rich composition can include no more than about 50% C5 sugars, nor more than about 40% C5 sugars, no more than about 30% C5 sugars, no more than about 20% C5 sugars, no more than about 10% C5 sugars, no more than about 5% C5 sugars, or it can include from about 2% to about 10% C5 sugars by weight.

A "liquid" composition may contain solids and a "solids" composition may contain liquids. A liquid composition refers to a composition in which the material is primarily liquid, and a solids composition is one in which the material is primarily solid.

The terms "non-cellulosic" and "sugar- or starch-based" are used interchangeably and have the same meaning. For example "non-cellulosic fermentation process" is used interchangeably and means the same thing as "sugar- and starch-based fermentation process." Starch is a carbohydrate consisting of consisting of a large number of glucose units joined by glycosidic bonds. The glycosidic bonds are typically the easily hydrolysable alpha glycosidic bonds. This polysaccharide can be produced by all green plants as an energy store. There can be two types of starch molecules: the linear and helical amylose and the branched amylopectin, although amylase can also contain branches.

DESCRIPTION

The following description and examples illustrate some exemplary embodiments of the disclosure in detail. Those of skill in the art will recognize that there are numerous variations and modifications of this disclosure that are encompassed by its scope. Accordingly, the description of a certain exemplary embodiment should not be deemed to limit the scope of the present disclosure.

When timber is cut in a mill, the cut timber is accounted for and a certain yield per log and stock deduction can be formed. A logging company can cut over 200,000 cords of wood each year. The waste products, however, are not usually very useful. They consist of wood chips, slash, bark, sawdust, and other materials than the wood itself. The wood consists of lignin-reinforced vessels, phloem, tracheids, and fibers. There is also a lot of debris around cutting sites and mills. Some of this material is used to power the mills; e.g., by burning. Some of it can be sold but has to be shipped out to potential buyers. Demand for wood and paper products determines the residual price forest landowners receive for harvested trees. If the price is not high enough to cover the costs of production, the landowner may not harvest the timber, and if the timber is harvested, the landowner likely won't invest in growing the next cycle. Further, landowners in many states are required to promptly reforest a harvested area, but site preparation by slash burning is becoming uncommon due to cost and air-quality concerns.

The U.S. as a whole is the world's largest producer of forest products and the world's largest consumer as well, accounting for roughly one-quarter to one-third of both world production and consumption. In some states, such as Maine, there are an estimated over 200 logging companies and lumber mills and most are located in remote areas. Throughout the United States and Canada alone, there are thousands of logging operations, sawmills and paper mills. These are hardwood and softwood mills, pulp mills for paper production, plywood mills and engineered wood processors (hereinafter "mills"). These mills are declining in numbers partly because of the older, inefficient small sawmills that relied on large, old-growth logs and were not very accessible to transportation. Newer larger mills are more productive and closer to transportation centers but not necessarily to the sites of timber harvesting. Thus it is costly to transport cut timber to these sites. It is even more costly to convey slash and chips from cutting operations.

It is known to use a variety of different types of feedstock to produce ethanol. It is also known to utilize a number of different methods for processing feedstock into ethanol. However, each of the different conventional methods suffer from one or more disadvantages, regardless, of the type of feedstock used to produce ethanol. For example, conventional methods for producing ethanol require raw, unprocessed feedstock to be transported from the site where the feedstock is produced or stored to a remote processing plant. Transportation of raw, unprocessed feedstock from the site of the feedstock producer to the ethanol producing plant results in substantial equipment, labor, fuel, maintenance and repair costs. More particularly, the transportation of raw, unprocessed feedstock results in an ethanol yield (by weight) of approximately 33% of the feedstock (by weight). In addition, the transportation of raw, unprocessed feedstock results in byproduct at the ethanol producing plant which amounts to approximately 33% (by weight) of the feedstock (by weight). Additional transportation costs, including labor, fuel, maintenance and repair, are incurred in connection with the removal of the byproducts from the ethanol producing plant. Further, conventional methods for producing ethanol require large storage capacities at either or both the site of the feedstock producer and the ethanol producing plant.

It would be desirable, therefore, if a method and system for producing ethanol could be provided that reduces the transportation costs associated with the production of ethanol from feedstock. It would also be desirable such a method and system could be provided that would reduce the tonnage of feedstock transported from a feedstock provider to an ethanol producer. It would be further desirable if such a method and system could be provided that would produce byproducts that may be left at the site of the feedstock provider to be used as animal feed, animal bedding, compost, biofuel, chemicals or the like. It would be a still further desirable if such a method and system could be provided that would produce a non-hazardous material to be transported from the feedstock provider to the ethanol producer. It would also be desirable if such a method and system could be provided that would reduce the storage requirements at an ethanol producing plant. It would be further desirable if such a method and system could be provided that would reduce or eliminate the environmental impact caused by the storage of feedstock, the disposal of byproducts, waste products and waste water, and the transportation of feedstock to an ethanol producing plant. It would be still further desirable if such a method and system could be produced that would reduce the size and cost of an ethanol producing plant and improve the efficiency of such a plant.

It is an advantage of the preferred embodiments of the invention to provide a method and system for producing ethanol that reduces the transportation costs associated with the production of ethanol from feedstock. It is also an advantage of the preferred embodiments to provide a method and system that reduces the tonnage of feedstock transported from a feedstock provider to an ethanol producer. It is another advantage of the preferred embodiments to provide a method and system that produces byproducts that may be left at the site of the feedstock provider to be used as animal feed, animal bedding, compost, biofuel, chemicals or the like. It is still another advantage of the preferred embodiment to provide a method and system that produces a non-hazardous material to be transported from the feedstock provider to the ethanol producer. It yet another advantage of the preferred embodiments to provide a method and system that reduces the storage requirements at the ethanol producing plant. It is a further advantage of the preferred embodiments to provide a method and system that reduces or eliminates the environmental impact caused by the storage of feedstock, the disposal of byproducts, waste products and waste water, and the transportation of feedstock to an ethanol producing plant. It is a still further advantage of the preferred embodiments to provide a method and system that reduces the size and cost of an ethanol producing plant and improve the efficiency of such a plant.

Other advantages and features of this invention will become apparent from an examination of the drawings and the ensuing description.

Disclosed herein are methods to reduce the cost of mill operations by integrating portable pretreatment equipment with wood processing so that byproducts are utilized productively at the mill sites as commercial intermediates and/or end products are synthesized.

In one embodiment, a system is provided to establish one or more portable pretreatment units at a mill to process slash, wood chips, and the like. The pretreatment process utilizes the lignocellulosic and hemicellulosic biomass and extracts the C5 and C6 sugars that can be concentrated into 15-50% sugar solutions or even extracted to powder or crystalline form for transport to biofuel or chemical plants. These sugar intermediates are more valuable than wood chips and other byproducts and can be part of the profit of the mill operations.

FIG. 1 is a representation of the type of operation that includes a pretreatment unit with a pulp mill operation. Following harvest of timber 1, lignocellulosic chips and slash 2 can be collected for processing into an end product. The timber is debarked at the mill and the bark 3 is used to extract chemicals or produce energy 5. The wood from the debarked logs is then cut into chips 4 which can be used for pulping 6 and production of paper 7 while the chemical extractives and waste 8 are processed further into wood extractives and other chemicals 9. Chips 4 and/or slash 2 or other lignocellulosic bioproducts are transferred to the portable pretreatment units 10 where this biomass is pretreated as described infra. Following enzymatic hydrolysis the monomeric sugars produced can be further processed in a fermentation unit 11 and the end product concentrated or separated as required to produce one or more biofuels 12 or another chemical 13.

In an alternative embodiment, the sugars produced from the lignocellulosic biomass are concentrated to a sugar solution containing from 10% to 80% sugar (wt/vol) or completely dried to a solid form, so that the sugar are easily and inexpensively conveyed to another facility for fermentation into an end product. The pretreatment units can be transported to any type of mill where the feedstock is adequate for producing sugars. The lignin that is produced through pretreatment (or pulping) is used to produce energy (through combustion) to run the mill or can be further transported for animal feed or other purposes.

Figure 2:
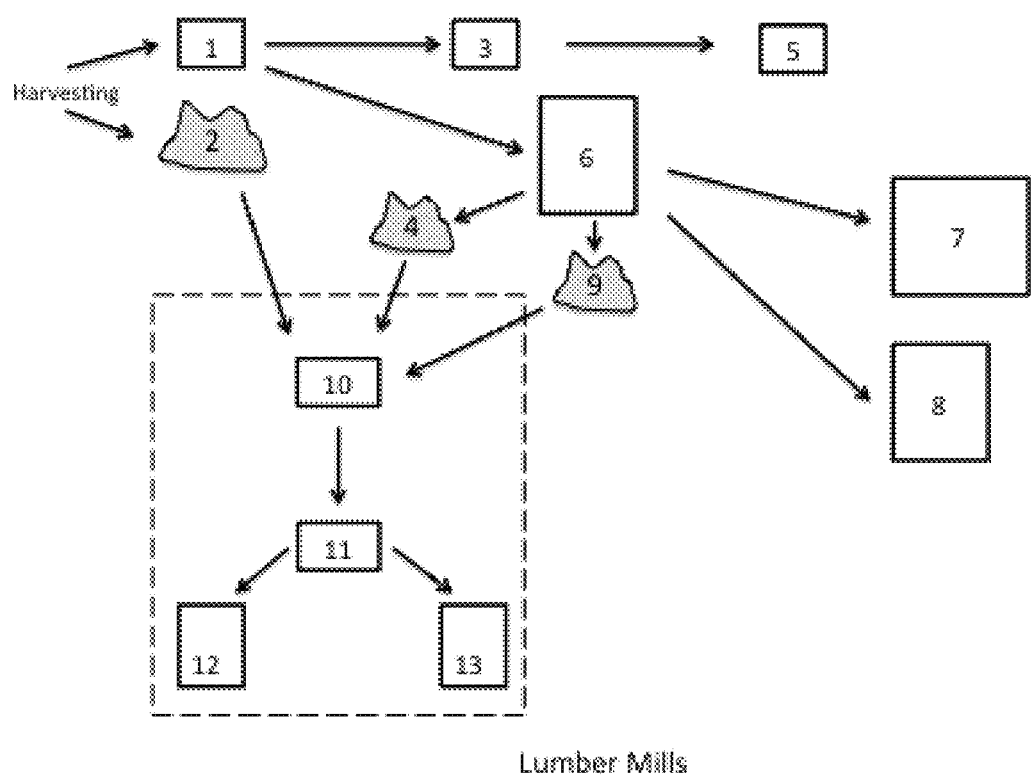
FIG. 2 is a diagram depicting a system for producing sugar hydrolysate products from wood residues at a lumber mill.

FIG. 2 is a representation of the type of operation that includes a pretreatment unit with a lumber mill operation. Following harvest of timber 1, lignocellulosic chips and slash 2 can be collected for processing into an end product. The timber is debarked at the mill and the bark 3 is used to extract chemicals or produce energy 5. The wood from the debarked logs 6 is then cut into boards 7 and slats 8 which can be used for construction and other purposes. Chips 4 and sawdust 9 and/or other lignocellulosic byproducts are transferred to the portable pretreatment units 10 where this biomass is pretreated as described infra. Following enzymatic hydrolysis, the monomeric sugars produced can be further processed in a fermentation unit 11 and the end product concentrated or separated as required to produce one or more biofuels 12 or another chemical 13.

In an alternative embodiment, the sugars produced from the lignocellulosic biomass during lumbering operations are concentrated to a sugar solution containing from 10% to 80% sugar (wt/vol) or completely dried to a solid form, so that the sugars are easily and inexpensively transported to another facility for fermentation into an end product.

The pretreatment units can be moved to any type of mill where the feedstock is adequate for producing sugars and the systems set up to produce sugar from lignocellulosic byproducts. The lignin that is produced through pretreatment (or pulping) is used to produce energy (through combustion) to run the mill or can be further transported for animal feed or other purposes.

The advantage of portable biomass pretreatment units is that access to pretreatment is available practically anywhere for any period of time without expensive construction of pretreatment plants. Any type of lignocellulosic biomass or biomass comprising cellulosic or hemicellulosic material can be pretreated in these units. Thus a pretreatment unit that is able to convert 10-40 tons of lignocellulosic material into sugars per day can be transported to a timber harvesting site and operational within days. It can also be disassembled in the same period of time and taken to another harvesting site. Units that process from 10 to 1000 tons of biomass/day are transportable and more than one unit can be assembled to handle even larger biomass tonnage at a single site.

Figure 3:
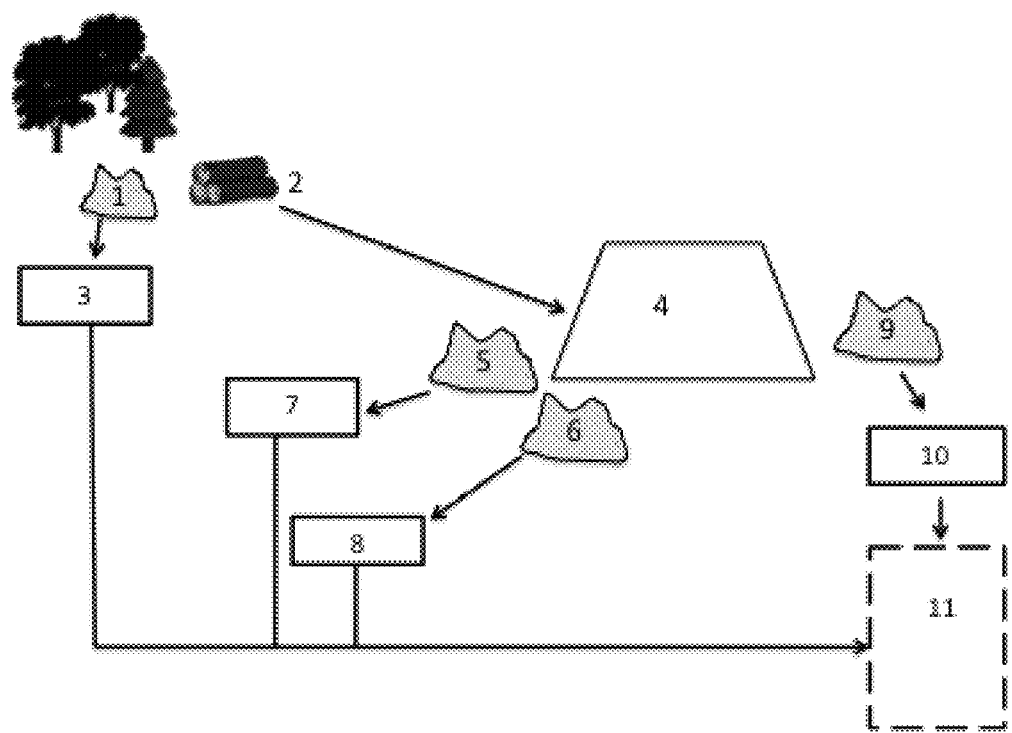
FIG. 3 is a diagram depicting the use of portable pretreatment units at timber processing sites.

As an example, without meaning to be limiting, FIG. 3 shows the use of four pretreatment units at a site of a mill. The mill can be a lumber, pulp and paper, plywood, or other wood-processing facility. A pretreatment unit 3 is used to pretreat wood slash, dead wood, or slash at a forestry site. When logs 2 are produced from the timber, they are transported to a mill where wood debris 5, wood chips 6, or sawdust 9 is produced during mill operations. Several different size pretreatment units are used to handle the woody waste. Pretreatment unit 7 can handle woody biomass from initial operations such as debarking or cleanup of logs, pretreatment unit 8 can handle wood chips produced during chipping or cutting of logs, and pretreatment unit 10 can process sawdust or other woody materials produced as a final product is made at the mill. The number and size of the pretreatment units can vary with the amount of woody waste produced that can be converted to sugars.

Following pretreatment, the sugar products are transported to a fermentation plant 11 for conversion into biofuels or chemicals. Alternatively, an ethanol or other biofuel/chemical plant can be constructed at the mill site. This would provide either fuel for operation of the mill, thus obviating the need to burn slash and wood chips, or the end product of the plant could be transported to a buyer. The cost of transportation of tons of raw biomass material would be eliminated and the reduced cost of transportation of biofuel or chemical product would result in an overall savings compared to traditional mill operations. In fact, during times when lumber prices are low, more production can be transferred to extracting fuel or other end products from the lumber itself.

Feedstock and Pretreatment of Feedstock

In one embodiment, the feedstock (biomass) contains cellulosic, hemicellulosic, and/or lignocellulosic material. The feedstock can be derived from trees, woodchips, slash, sawdust, paper, pulp, cardboard, waste and other sources.

Cellulose is a linear polymer of glucose where the glucose units are connected via $\beta(1\rightarrow4)$ linkages. Hemicellulose is a branched polymer of a number of sugar monomers including glucose, xylose, mannose, galactose, rhamnose and arabinose, and can have sugar acids such as mannuronic acid and galacturonic acid present as well. Lignin is a cross-linked, racemic macromolecule of mostly p-coumaryl alcohol, coniferyl alcohol and sinapyl alcohol. These three polymers occur together in lignocellusic materials in plant biomass. The different characteristics of the three polymers can make hydrolysis of the combination difficult as each polymer tends to shield the others from enzymatic attack.

In one embodiment, methods are provided for the pretreatment of feedstock used in the fermentation and production of the biofuels and chemicals. The pretreatment steps can include mechanical, thermal, pressure, chemical, thermochemical, and/or biochemical tests pretreatment prior to being used in a bioprocess for the production of fuels and chemicals, but untreated biomass material can be used in the process as well. Mechanical processes can reduce the particle size of the biomass material so that it can be more conveniently handled in the bioprocess and can increase the surface area of the feedstock to facilitate contact with chemicals/biochemicals/biocatalysts. Mechanical processes can also separate one type of biomass material from another. The biomass material can also be subjected to thermal and/or chemical pretreatments to render plant polymers more accessible. Multiple steps of treatment can also be used.

Mechanical processes include, are not limited to, washing, soaking, milling, size reduction, screening, shearing, size classification and density classification processes. Chemical processes include, but are not limited to, bleaching, oxidation, reduction, acid treatment, base treatment, sulfite treatment, acid sulfite treatment, basic sulfite treatment, ammonia treatment, and hydrolysis. Thermal processes include, but are not limited to, sterilization, ammonia fiber expansion or explosion ("AFEX"), steam explosion, holding at elevated temperatures, pressurized or unpressurized, in the presence or absence of water, and freezing. Biochemical processes include, but are not limited to, treatment with enzymes, including enzymes produced by genetically-modified plants, and treatment with microorganisms. Various enzymes that can be utilized include cellulase, amylase, β-glucosidase, xylanase, gluconase, and other polysaccharases; lysozyme; laccase, and other lignin-modifying enzymes; lipoxygenase, peroxidase, and other oxidative enzymes; proteases; and lipases. One or more of the mechanical, chemical, thermal, thermochemical, and biochemical processes can be combined or used separately. Such combined processes can also include those used in the production of paper, cellulose products, microcrystalline cellulose, and cellulosics and can include pulping, kraft pulping, acidic sulfite processing. The feedstock can be a side stream or waste stream from a facility that utilizes one or more of these processes on a biomass material, such as cellulosic, hemicellulosic or lignocellulosic material. Examples include paper plants, cellulosics plants, distillation plants, cotton processing plants, and microcrystalline cellulose plants. The feedstock can also include cellulose-containing or cellulosic containing waste materials. The feedstock can also be biomass materials, such as wood, grasses, corn, starch, or sugar, produced or harvested as an intended feedstock for production of ethanol or other products such as by biocatalysts.

In another embodiment, a method can utilize a pretreatment process disclosed in U.S. Patents and Patent Applications US20040152881, US20040171136, US20040168960, US20080121359, US20060069244, US20060188980, US20080176301, U.S Pat. Nos. 5,693,296, 6,262,313, US20060024801, U.S. Pat. Nos. 5,969,189, 6,043,392, US20020038058, U.S. Pat. Nos.5,865,898, 5,865,898, 6,478,965, 5,986,133, or US20080280338, each of which is incorporated by reference herein in its entirety.

In another embodiment, the AFEX process is be used for pretreatment of biomass. In a preferred embodiment, the AFEX process is used in the preparation of cellulosic, hemicellulosic or lignocellulosic materials for fermentation to ethanol or other products. The process generally includes combining the feedstock with ammonia, heating under pressure, and suddenly releasing the pressure. Water can be present in various amounts. The AFEX process has been the subject of numerous patents and publications.

In another embodiment, the pretreatment of biomass comprises the addition of calcium hydroxide to a biomass to render the biomass susceptible to degradation. Pretreatment comprises the addition of calcium hydroxide and water to the biomass to form a mixture, and maintaining the mixture at a relatively high temperature. Alternatively, an oxidizing agent, selected from the group consisting of oxygen and oxygen-containing gasses, can be added under pressure to the mixture. Examples of carbon hydroxide treatments are disclosed in U.S. Pat. No. 5,865,898 to Holtzapple and S. Kim and M. T. Holzapple, Bioresource Technology, 96, (2005) 1994, incorporated by reference herein in its entirety.

In one embodiment, pretreatment of biomass comprises dilute acid hydrolysis. Example of dilute acid hydrolysis treatment are disclosed in T. A. Lloyd and C. E Wyman, Bioresource Technology, (2005) 96, 1967), incorporated by reference herein in its entirety.

In another embodiment, pretreatment of biomass comprises pH controlled liquid hot water treatment. Examples of pH controlled liquid hot water treatments are disclosed in N. Mosier et al., Bioresource Technology, (2005) 96, 1986, incorporated by reference herein in its entirety.

In one embodiment, pretreatment of biomass comprises aqueous ammonia recycle process (ARP). Examples of aqueous ammonia recycle process are described in T. H. Kim and Y. Y. Lee, Bioresource Technology, (2005) 96, 2007, incorporated by reference herein in its entirety.

In one embodiment, the above-mentioned methods have two steps: a pretreatment step that leads to a wash stream, and an enzymatic hydrolysis step of pretreated-biomass that produces a hydrolysate stream. In the above methods, the pretreatment step can include acid hydrolysis, hot water pretreatment, steam explosion or alkaline reagent based methods (AFEX, ARP, and lime pretreatments). Dilute acid and hot water treatment methods can be used to solubilize all or a portion of the hemicellulose. Methods employing alkaline reagents can be used remove all, most, or a portion of the lignin during the pretreatment step. As a result, the wash stream from the pretreatment step in the former methods contains mostly hemicellulose-based sugars, whereas this stream has mostly lignin for the high-pH methods. The subsequent enzymatic hydrolysis of the residual biomass leads to mixed sugars (C5 and C6) in the alkali based pretreatment methods, while glucose is the major product in the hydrolyzate from the low and neutral pH methods. In one embodiment, the treated material is additionally treated with catalase or another similar chemical, chelating agents, surfactants, and other compounds to remove impurities or toxic chemicals or further release polysaccharides.

The biomass can be pretreated according to any of the methods disclosed herein; for example, by dilute acid, hot water treatment, stream explosion, or an alkaline pretreatment. The biomass can be pretreated using a combination of techniques; for example, the biomass can be pretreated using hot water or stream explosion followed by alkaline treatment.

In one embodiment, pretreatment of biomass comprises ionic liquid (IL) pretreatment. Biomass can be pretreated by incubation with an ionic liquid, followed by IL extraction with a wash solvent such as alcohol or water. The treated biomass can then be separated from the ionic liquid/wash-solvent solution by centrifugation or filtration, and sent to the saccharification reactor or vessel. Examples of ionic liquid pretreatment are disclosed in US publication No. 2008/0227162, incorporated herein by reference in its entirety.

In another embodiment, a method can utilize a pretreatment process disclosed in U.S. Pat. No. 4,600,590 to Dale, U.S. Pat. No. 4,644,060 to Chou, U.S. Pat. No. 5,037,663 to Dale. U.S. Pat. No. 5,171,592 to Holtzapple, et al., U.S. Pat. No. 5,939,544 to Karstens, et al., U.S. Pat. No. 5,473,061 to Bredereck, et al., U.S. Pat. No. 6,416,621 to Karstens, U.S. Pat. No. 6,106,888 to Dale, et al., U.S. Pat. No. 6,176,176 to Dale, et al., PCT publication WO2008/020901 to Dale, et al., Felix, A., et al., Anim. Prod. 51, 47-61 (1990), Wais, A. C., Jr., et al., Journal of Animal Science, 35, No. 1, 109-112 (1972), which are incorporated herein by reference in their entireties.

Alteration of the pH of a pretreated feedstock can be accomplished by washing the feedstock (e.g., with water) one or more times to remove an alkaline or acidic substance, or other substance used or produced during pretreatment. Washing can comprise exposing the pretreated feedstock to an equal volume of water 2, 3, 4, 5, 6, 7, 8, 9, 10, 11, 12, 13, 14, 15, 16, 17, 18, 19, 20, 21, 22, 23, 24, 25 or more times. In another embodiment, a pH modifier can be added. For example, an acid, a buffer, or a material that reacts with other materials present can be added to modulate the pH of the feedstock. In one embodiment, more than one pH modifier can be used, such as one or more bases, one or more bases with one or more buffers, one or more acids, one or more acids with one or more buffers, or one or more buffers. When more than one pH modifiers are utilized, they can be added at the same time or at different times. Other non-limiting exemplary methods for neutralizing feedstocks treated with alkaline substances have been described, for example in U.S. Pat. Nos. 4,048,341; 4,182,780; and 5,693,296.

In one embodiment, one or more acids can be combined, resulting in a buffer. Suitable acids and buffers that can be used as pH modifiers include any liquid or gaseous acid that is compatible with the microorganism. Non-limiting examples include $SO_2$ or sulfurous acid, peroxyacetic acid, sulfuric acid, lactic acid, citric acid, oxalic acid, phosphoric acid, and hydrochloric acid. In some instances, the pH can be lowered to neutral pH or acidic pH, for example a pH of 7.0, 6.5, 6.0, 5.5, 5.0, 4.5, 4.0, or lower. In some embodiments, the pH is lowered and/or maintained within a range of about pH 4.5 to about 7.1, or about 4.5 to about 6.9, or about pH 5.0 to about 6.3, or about pH 5.5 to about 6.3, or about pH 6.0 to about 6.5, or about pH 5.5 to about 6.9 or about pH 6.2 to about 6.7.

In another embodiment, biomass can be pre-treated at an elevated temperature and/or pressure. In one embodiment, at stage one or stage two, biomass is pre treated at a temperature range of 20° C. to 400° C. In another embodiment, biomass is pretreated at a temperature of about 20° C., 25° C., 30° C., 35° C., 40° C., 45° C., 50° C., 55° C., 60° C., 65° C., 80° C., 90° C., 100° C., 120° C., 150° C., 200° C., 250° C., 300° C., 350° C., 400° C. or higher. In another embodiment, elevated temperatures are provided by the use of steam, hot water, or hot gases. In one embodiment, steam can be injected into a biomass containing vessel. In another embodiment, the steam, hot water, or hot gas can be injected into a vessel jacket such that it heats, but does not directly contact the biomass.

In another embodiment, a biomass can be treated at an elevated pressure. In one embodiment, biomass is pre treated at a pressure range of about 1 psi to about 30 psi. In another embodiment, biomass is pre treated at a pressure or about 1 psi, 2 psi, 3 psi, 4 psi, 5 psi, 6 psi, 7 psi, 8 psi, 9 psi, 10 psi, 12 psi, 15 psi, 18 psi, 20 psi, 22 psi, 24 psi, 26 psi, 28 psi, 30 psi or more. In some embodiments, biomass can be treated with elevated pressures by the injection of steam into a biomass containing vessel. In one embodiment, the biomass can be treated to vacuum conditions prior or subsequent to alkaline or acid treatment or any other treatment methods provided herein.

In one embodiment, alkaline or acid pretreated biomass is washed (e.g. with water (hot or cold) or other solvent such as alcohol (e.g. ethanol)), pH neutralized with an acid, base, or buffering agent (e.g. phosphate, citrate, borate, or carbonate salt) or dried prior to fermentation. In one embodiment, the drying step can be performed under vacuum to increase the rate of evaporation of water or other solvents. Alternatively, or additionally, the drying step can be performed at elevated temperatures such as about 20° C., 25° C., 30° C., 35° C., 40° C., 45° C., 50° C., 55° C., 60° C., 65° C., 80° C., 90° C., 100° C., 120° C., 150° C., 200° C., 250° C., 300° C. or more.

In one embodiment, the pretreatment step includes a step of solids recovery at each stage. The solids recovery step can be during or also after pretreatment (e.g., acid or alkali pretreatment), or before the drying step. In one embodiment, the solids recovery step can include the use of a sieve, filter, screen, or a membrane for separating the liquid and solids fractions. In one embodiment, a suitable sieve pore diameter size ranges from about 0.001 microns to 8 mm, such as about 0.005 microns to 3 mm or about 0.01 microns to 1 mm. In one embodiment, a sieve pore size has a pore diameter of about 0.01 microns, 0.02 microns, 0.05 microns, 0.1 microns, 0.5 microns, 1 micron, 2 microns, 4 microns, 5 microns, 10 microns, 20 microns, 25 microns, 50 microns, 75 microns, 100 microns, 125 microns, 150 microns, 200 microns, 250 microns, 300 microns, 400 microns, 500 microns, 750 microns, 1 mm or more. In one embodiment, biomass (e.g. corn stover) is processed or pretreated prior to fermentation. In one embodiment, a method of pre-treatment includes but is not limited to, biomass particle size reduction, such as for example shredding, milling, chipping, crushing, grinding, or pulverizing. In one embodiment, biomass particle size reduction can include size separation methods such as sieving, or other suitable methods known in the art to separate materials based on size. In one embodiment, size separation can provide for enhanced yields. In one embodiment, separation of finely shredded biomass (e.g. particles smaller than about 8 mm in diameter, such as, 8, 7.9, 7.7, 7.5, 7.3, 7, 6.9, 6.7, 6.5, 6.3, 6, 5.9, 5.7, 5.5, 5.3, 5, 4.9, 4.7, 4.5, 4.3, 4, 3.9, 3.7, 3.5, 3.3, 3, 2.9, 2.7, 2.5, 2.3, 2, 1.9, 1.7, 1.5, 1.3, 1, 0.9, 0.8, 0.7, 0.6, 0.5, 0.4, 0.3, 0.2, or 0.1 mm) from larger particles allows the recycling of the larger particles back into the size reduction process, thereby increasing the final yield of processed biomass. In one embodiment, a fermentative mixture is provided which comprises a pretreated lignocellulosic feedstock comprising less than about 50% of a lignin component present in the feedstock prior to pretreatment and comprising more than about 60% of a hemicellulose component present in the feedstock prior to pretreatment; and a microorganism capable of fermenting a five-carbon sugar, such as xylose, arabinose or a combination thereof, and a six-carbon sugar, such as glucose, galactose, mannose or a combination thereof. In some instances, pretreatment of the lignocellulosic feedstock comprises adding an alkaline substance which raises the pH to an alkaline level, for example NaOH. In one embodiment, NaOH is added at a concentration of about 0.5% to about 2% by weight of the feedstock. In one embodiment, pretreatment also comprises addition of a chelating agent.

Hydrolysis

In one embodiment, a biomass hydrolyzing unit provides useful advantages for the conversion of biomass to biofuels and chemical products. One advantage of this unit is its ability to produce monomeric sugars from multiple types of biomass, including mixtures of different biomass materials, and is capable of hydrolyzing polysaccharides and higher molecular weight saccharides to lower molecular weight saccharides. In one embodiment, the hydrolyzing unit utilizes a pretreatment process and a hydrolytic enzyme which facilitates the production of a sugar stream containing a concentration of a monomeric sugar or several monomeric sugars derived from cellulosic and/or hemicellulosic polymers. Examples of biomass material that can be pretreated and hydrolyzed to manufacture sugar monomers include, but are not limited to, cellulosic, hemicellulosic, lignocellulosic materials; pectins; starches; wood; paper; agricultural products; forest waste; tree waste; tree bark; leaves; grasses; sawgrass; woody plant matter; non-woody plant matter; carbohydrates; starch; inulin; fructans; glucans; corn; hulls; sugar cane; sorghum, other grasses; bamboo, algae, and material derived from these materials. This ability to use a very wide range of pretreatment methods and hydrolytic enzymes gives distinct advantages in biomass fermentations. Various pretreatment conditions and enzyme hydrolysis can enhance the extraction of sugars from biomass, resulting in higher yields, higher productivity, greater product selectivity, and/or greater conversion efficiency.

In one embodiment, the enzyme treatment is used to hydrolyze various higher saccharides (higher molecular weight) present in biomass to lower saccharides (lower molecular weight), such as in preparation for fermentation by biocatalysts such as yeasts to produce ethanol, hydrogen, or other chemicals such as organic acids including succinic acid, formic acid, acetic acid, and lactic acid. These enzymes and/or the hydrolysate can be used in fermentations to produce various products including fuels, and other chemicals.

In one example, the process for converting biomass material into ethanol includes pretreating the biomass material (e.g., "feedstock"), hydrolyzing the pretreated biomass to convert polysaccharides to oligosaccharides, further hydrolyzing the oligosaccharides to monosaccharides, and converting the monosaccharides to biofuels and chemical products. This process is repeated in the second stage. Enzymes such as cellulases, polysaccharases, lipases, proteases, ligninases, and hemicellulases, help produce the monosaccharides can be used in the biosynthesis of fermentation end-products. Biomass material that can be utilized includes woody plant matter, non-woody plant matter, cellulosic material, lignocellulosic material, hemicellulosic material, carbohydrates, pectin, starch, inulin, fructans, glucans, corn, hulls, distiller's grains, algae, sugarcane, other grasses, switchgrass, bagasse, wheat straw, barley straw, rice straw, corncobs, bamboo, citrus peels, sorghum, high biomass sorghum, seed hulls, and material derived from these. The final product can then be separated and/or purified, as indicated by the properties for the desired final product. In some instances, compounds related to sugars such as sugar alcohols or sugar acids can be utilized as well.

Chemicals that can be used in the methods disclosed herein can be purchased from a commercial supplier, such as Sigma-Aldrich. Additionally, commercial enzyme cocktails (e.g. Accellerase™ 1000, CelluSeb-TL, CelluSeb-TS, Cellic™, CTec, STARGEN™, Maxalig™ Spezyme®, Distillase®, G-Zyme®, Fermenzyme®, Fermgen™, GC 212, or Optimash™) or any other commercial enzyme cocktail can be purchased from vendors such as Specialty Enzymes & Biochemicals Co., Genencor, or Novozymes. Alternatively, enzyme cocktails can be prepared by growing one or more organisms such as for example a fungi (e.g. a *Trichoderma*, a *Saccharomyces*, a *Pichia*, a White Rot Fungus etc.), a bacteria (e.g. a *Clostridium*, or a coliform bacterium, a *Zymomonas* bacterium, *Sacharophagus degradans* etc.) in a suitable medium and harvesting enzymes produced therefrom. In some embodiments, the harvesting can include one or more steps of purification of enzymes.

In one embodiment, treatment of biomass comprises enzyme hydrolysis. In one embodiment, a biomass is treated with an enzyme or a mixture of enzymes, e.g., endoglucanases, exoglucanases, cellobiohydrolases, cellulase, beta-glucosidases, glycoside hydrolases, glycosyltransferases, lyases, esterases, amylases, glucoamylases, and proteins containing carbohydrate-binding modules. In one embodiment, the enzyme or mixture of enzymes is one or more individual enzymes with distinct activities. In another embodiment, the enzyme or mixture of enzymes can be enzyme domains with a particular catalytic activity. For example, an enzyme with multiple activities can have multiple enzyme domains, including for example glycoside hydrolases, glycosyltransferases, lyases and/or esterases catalytic domains. In another aspect, provided is a method for producing fermentation end products by: reducing a biomass material to a high percentage of homogeneous particles less than 1.5 mm in size; pretreating the biomass to release a C5 fraction and a C6 fraction; separating said C5 fraction from said C6 fraction; and hydrolyzing the C5 and C6 fractions with enzymes wherein the C5 fraction is hydrolyzed with one or more hemicellulase and the C6 fraction is hydrolyzed with one or more cellulase. In one embodiment, the percentage of homogeneous particles is 95% or greater, 90% or greater, 85% or greater, 80% or greater, 75% or greater, 70% or greater, 65% or greater, 60% or greater, 55% or greater, 50% or greater, 45% or greater, 40% or greater, 35% or greater, or 30% or greater.

In a further aspect, provided is a method of producing sugar polymers and oligomers and hydrolyzing this material with a 0.25-0.90% v/w enzyme addition; collecting enzymatically-released sugars in the solution; and fermenting the sugars with a biocatalyst to produce a fermentation end product. In one embodiment, the C5 fraction is separated from the C6 fraction during pretreatment. In another embodiment, the C5 fraction is enzymatically hydrolyzed separately from the C6 fraction. In another embodiment, the total enzyme added to hydrolyze the C5 fraction is 0.25-0.9% of the normal volume of enzymes. In another embodiment, the total enzyme added to hydrolyze the C6fraction is 0.25-0.9% of the normal volume of enzymes. In one embodiment, the total enzyme added to hydrolyze the C5 fraction is 0.20%, 0.25%, 0.30%, 0.35%, 0.40%, 0.45%, 0.50%, 0.55%, 0.60%, 0.65%, 0.70%, 0.75%, 0.80%, 0.85%, 0.90% of the normal volume of enzymes. In one embodiment, the total enzyme added to hydrolyze the C6 fraction is 0.20%, 0.25%, 0.30%, 0.35%, 0.40%, 0.45%, 0.50%, 0.55%, 0.60%, 0.65%, 0.70%, 0.75%, 0.80%, 0.85%, 0.90% of the normal volume of enzymes.

In one embodiment, enzymes that degrade polysaccharides are used for the hydrolysis of biomass and can include enzymes that degrade cellulose, namely, cellulases. Examples of some cellulases include endocellulases and exo-cellulases that hydrolyze beta-1,4-glucosidic bonds.

In one embodiment, enzymes that degrade polysaccharides are used for the hydrolysis of biomass and can include enzymes that have the ability to degrade hemicellulose, namely, hemicellulases. Hemicellulose can be a major component of plant biomass and can contain a mixture of pentoses and hexoses, for example, D-xylopyranose, L-arabinofuranose, D-mannopyranose, D-glucopyranose, D-galactopyranose, D-glucopyranosyluronic acid and other sugars. In one embodiment, enzymes that degrade polysaccharides are used for the hydrolysis of biomass and can include enzymes that have the ability to degrade pectin, namely, pectinases. In plant cell walls, the cross-linked cellulose network can be embedded in a matrix of pectins that can be covalently cross-linked to xyloglucans and certain structural proteins. Pectin can comprise homogalacturonan (HG) or rhamnogalacturonan (RH).

In one embodiment, after pretreatment and/or hydrolysis by any of the above methods the feedstock contains cellulose, hemicellulose, soluble oligomers, simple sugars, lignin, volatiles and ash. The parameters of the hydrolysis can be changed to vary the concentration of the components of the pretreated feedstock. For example, a hydrolysis can be chosen so that the concentration of soluble C5 saccharides is high and the concentration of lignin is low after hydrolysis. Examples of parameters of the hydrolysis include temperature, pressure, time, concentration, composition and pH.

In one embodiment, the parameters of the pretreatment and hydrolysis are changed to vary the concentration of the components of the pretreated feedstock such that concentration of the components in the pretreated and hydrolyzed feedstock is optimal for fermentation with a microbe such as a yeast or bacterium microbe.

In one embodiment, the parameters of the pretreatment are changed to encourage the release of the components of a genetically modified feedstock such as enzymes stored within a vacuole to increase or complement the enzymes synthesized by biocatalyst to produce optimal release of the fermentable components during hydrolysis and fermentation.

In one embodiment, the parameters of the pretreatment and hydrolysis are changed such that concentration of accessible cellulose in the pretreated feedstock is 1%, 5%, 10%, 12%, 13%, 14%, 15%, 16%, 17%, 19%, 20%, 30%, 40% or 50%. In one embodiment, the parameters of the pretreatment are changed such that concentration of accessible cellulose in the pretreated feedstock is 5% to 30%. In one embodiment, the parameters of the pretreatment are changed such that concentration of accessible cellulose in the pretreated feedstock is 10% to 20%.

In one embodiment, the parameters of the pretreatment are changed such that concentration of hemicellulose in the pretreated feedstock is 1%, 5%, 10%, 12%, 13%, 14%, 15%, 16%, 17%, 19%, 20%, 21%, 22%, 23%, 24%, 25%, 26%, 27%, 28%, 29%, 30%, 40% or 50%. In one embodiment, the parameters of the pretreatment are changed such that concentration of hemicellulose in the pretreated feedstock is 5% to 40%. In one embodiment, the parameters of the pretreatment are changed such that concentration of hemicellulose in the pretreated feedstock is 10% to 30%.

In one embodiment, the parameters of the pretreatment and hydrolysis are changed such that concentration of soluble oligomers in the pretreated feedstock is 1%, 10%, 15%, 20%, 25%, 30%, 35%, 40%, 45%, 50%, 55%, 60%, 65%, 70%, 75%, 80%, 85%, 90%, 95%, or 99%. Examples of soluble oligomers include, but are not limited to, cellobiose and xylobiose. In one embodiment, the parameters of the pretreatment are changed such that concentration of soluble oligomers in the pretreated feedstock is 30% to 90%. In one embodiment, the parameters of the pretreatment and/or hydrolysis are changed such that concentration of soluble oligomers in the pretreated feedstock is 45% to 80%.

In one embodiment, the parameters of the pretreatment and hydrolysis are changed such that concentration of simple sugars in the pretreated feedstock is 1%, 5%, 10%, 12%, 13%, 14%, 15%, 16%, 17%, 19%, 20%, 30%, 40% or 50%. In one embodiment, the parameters of the pretreatment and hydrolysis are changed such that concentration of simple sugars in the pretreated feedstock is 0% to 20%. In one embodiment, the parameters of the pretreatment and hydrolysis are changed such that concentration of simple sugars in the pretreated feedstock is 0% to 5%. Examples of simple sugars include, but are not limited to, C5 and C6 monomers and dimers.

In one embodiment, the parameters of the pretreatment are changed such that concentration of lignin in the pretreated and/or hydrolyzed feedstock is 1%, 5%, 10%, 12%, 13%, 14%, 15%, 16%, 17%, 19%, 20%, 30%, 40% or 50%. In one embodiment, the parameters of the pretreatment and/or hydrolysis are changed such that concentration of lignin in the pretreated feedstock is 0% to 20%. In one embodiment, the parameters of the pretreatment and/or hydrolysis are changed such that concentration of lignin in the pretreated feedstock is 0% to 5%. In one embodiment, the parameters of the pretreatment and hydrolysis are changed such that concentration of lignin in the pretreated and/or hydrolyzed feedstock is less than 1% to 2%. In one embodiment, the parameters of the pretreatment and/or hydrolysis are changed such that the concentration of phenolics is minimized.

In one embodiment, the parameters of the pretreatment and/or hydrolysis are changed such that concentration of furfural and low molecular weight lignin in the pretreated and/or hydrolyzed feedstock is less than 10%, 9%, 8%, 7%, 6%, 5%, 4%, 3%, 2%, or 1%. In one embodiment, the parameters of the pretreatment and/or hydrolysis are changed such that concentration of furfural and low molecular weight lignin in the pretreated and/or hydrolyzed feedstock is less than 1% to 2%.

In one embodiment, the parameters of the pretreatment and/or hydrolysis are changed such that the concentration of simple sugars is at least 75% to 85%, and the concentration of lignin is 0% to 5% and the concentration of furfural and low molecular weight lignin in the pretreated feedstock is less than 1% to 2%.

In one embodiment, the parameters of the pretreatment and/or hydrolysis are changed to obtain a high concentration of hemicellulose and a low concentration of lignin. In one embodiment, the parameters of the pretreatment and/or hydrolysis are changed to obtain a high concentration of hemicellulose and a low concentration of lignin such that concentration of the components in the pretreated stock is optimal for fermentation with a microbe such as biocatalyst.

In one embodiment, more than one of these steps can occur at any given time. For example, hydrolysis of the pretreated feedstock and hydrolysis of the oligosaccharides can occur simultaneously, and one or more of these can occur simultaneously to the conversion of monosaccharides to a fuel or chemical.

In another embodiment, an enzyme can directly convert the polysaccharide to monosaccharides. In some instances, an enzyme can hydrolyze the polysaccharide to oligosaccharides and the enzyme or another enzyme can hydrolyze the oligosaccharides to monosaccharides.

In another embodiment, the enzymes can be added to the fermentation or they can be produced by microorganisms present in the fermentation. In one embodiment, the microorganism present in the fermentation produces some enzymes. In another embodiment, enzymes are produced separately and added to the fermentation.

For the overall conversion of pretreated biomass to final product to occur at high rates, the enzymes for each conversion step can be present with sufficiently high activity. If one of these enzymes is missing or is present in insufficient quantities, the production rate of an end product can be reduced. The production rate can also be reduced if the microorganisms responsible for the conversion of monosaccharides to product only slowly take up monosaccharides and/or have only limited capability for translocation of the monosaccharides and intermediates produced during the conversion to end product. Additions of fractions obtained from pretreatment and/or pretreatment and hydrolysis can increase initial or overall growth rates. In another embodiment, oligomers are taken up slowly by a biocatalyst, necessitating an almost complete conversion of polysaccharides and oligomers to monomeric sugars.

In another embodiment, the enzymes of the method are produced by a biocatalyst, including a range of hydrolytic enzymes suitable for the biomass materials used in the fermentation methods. In one embodiment, a biocatalyst is grown under conditions appropriate to induce and/or promote production of the enzymes needed for the saccharification of the polysaccharide present. The production of these enzymes can occur in a separate vessel, such as a seed fermentation vessel or other fermentation vessel, or in the production fermentation vessel where ethanol production occurs. When the enzymes are produced in a separate vessel, they can, for example, be transferred to the production fermentation vessel along with the cells, or as a relatively cell free solution liquid containing the intercellular medium with the enzymes. When the enzymes are produced in a separate vessel, they can also be dried and/or purified prior to adding them to the hydrolysis or the production fermentation vessel. The conditions appropriate for production of the enzymes are frequently managed by growing the cells in a medium that includes the biomass that the cells will be expected to hydrolyze in subsequent fermentation steps. Additional medium components, such as salt supplements, growth factors, and cofactors including, but not limited to phytate, amino acids, and peptides can also assist in the production of the enzymes utilized by the microorganism in the production of the desired products.

Fermentation

Provided herein are methods and compositions for a two-stage process of producing one or more fermentation products from feedstocks comprising one or more cellulosic and/or hemicellulosic polysaccharides. The source of the one or more polysaccharides can be a lignocellulosic feedstock. The fermentation product can be produced by two-stage pretreating and/or hydrolyzing a biomass comprising cellulose, hemicellulose, or lignocellulose.

Provided herein are methods and compositions for a two-stage process of producing one or more fermentation products from feedstocks comprising a mixture of non-cellulosic polysaccharides (e.g., starch) and one or more cellulosic and/or hemicellulosic polysaccharides. The source of the one or more polysaccharides can be a lignocellulosic feedstock. The fermentation product can be produced by two-stage pretreating and/or hydrolyzing a biomass comprising cellulose, hemicellulose, or lignocellulose.

Enhanced rates of fermentation can be achieved using a first stage process to hydrolyze hemicellulose and a second stage to hydrolyze cellulose in comparison to a one-stage pretreatment hydrolysis. The enhanced rates of fermentation can be from about 1% higher to about 100% higher; for example, about 1-100%, 1-75%, 1-50%, 1-25%, 1-10%, 10-100%, 10-75%, 10-50%, 10-25%, 25-100%, 25-75%, 25-50%, 50-100%, 50-75%, 75-100%, 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 55%, 60%, 65%, 70%, 75%, 80%, 85%, 90%, 95%, or 100% higher.

Increased yields of one or more fermentation end-products can be achieved using lignocellulosic feedstocks pre-treated in a two-stage process in comparison to fermentation of lignocellulosic feedstock pretreated in a one-stage process. The increased yields of one or more fermentation end-products can be from about 1% higher to about 100% higher; for example, about 1-100%, 1-75%, 1-50%, 1-25%, 1-10%, 10-100%, 10-75%, 10-50%, 10-25%, 25-100%, 25-75%, 25-50%, 50-100%, 50-75%, 75-100%, 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 55%, 60%, 65%, 70%, 75%, 80%, 85%, 90%, 95%, or 100% higher.

In one embodiment, the concentration of monosaccharides at the start of a fermentation or simultaneous saccharification and fermentation reaction can be less than about 100 g/L; for example, less than about 100 g/L, 90 g/L, 80 g/L, 70 g/L, 60 g/L, 50 g/L, 40 g/L, 30 g/L, 25 g/L, 20 g/L, 15 g/L, 10 g/L, 9 g/L, 8 g/L, 7 g/L, 6 g/L, 5 g/L, 4 g/L, 3 g/L, 2 g/L, or 1 g/L. In another embodiment, the concentration of monosaccharides at the start of a fermentation or simultaneous saccharification and fermentation reaction can be from about 1 g/L to about 100 g/L; for example, about 1-100 g/L, 1-75 g/L, 1-50 g/L, 1-25 g/L, 1-10 g/L, 10-100 g/L, 10-75 g/L, 10-50 g/L, 10-25 g/L, 25-100 g/L, 25-75 g/L, 25-50 g/L, 50-100 g/L, 50-75 g/L, or 75-100 g/L.

The present disclosure also provides a fermentative mixture comprising: a cellulosic feedstock pre-treated with an acid substance and at a temperature of from about 80° C. to about 120° C.; subsequently hydrolyzed with an enzyme mixture, and a microorganism capable of fermenting a five-carbon sugar and/or a six-carbon sugar. In one embodiment, the five-carbon sugar is xylose, arabinose, or a combination thereof. In one embodiment, the six-carbon sugar is glucose, galactose, mannose, or a combination thereof. In one embodiment, the acid is equal to or less than 2% HCl or $SO_2$ or $H_2SO_4$. In one embodiment, the microorganism is a *Rhodococcus* strain, a *Clostridium* strain, a *Trichoderma* strain, a *Saccharomyces* strain, a *Zymomonas* strain, or another microorganism suitable for fermentation of biomass. In another embodiment, the fermentation process comprises fermentation of the biomass using a microorganism that is *Clostridium phytofermentans, Clostridium algidixylanolyticum, Clostridium xylanolyticum, Clostridium cellulovorans, Clostridium cellulolyticum, Clostridium thermocellum, Clostridium josui, Clostridium papyrosolvens, Clostridium cellobioparum, Clostridium hungatei, Clostridium cellulosi, Clostridium stercorarium, Clostridium termitidis, Clostridium thermocopriae, Clostridium celerecrescens, Clostridium polysaccharolyticum, Clostridium populeti, Clostridium lentocellum, Clostridium chartatabidum,*

*Clostridium aldrichii, Clostridium herbivorans, Acetivibrio cellulolyticus, Bacteroides cellulosolvens, Caldicellulosiruptor saccharolyticum, Rhodococcus opacus, Ruminococcus albus, Ruminococcus flavefaciens, Fibrobacter succinogenes, Eubacterium cellulosolvens, Butyrivibrio fibrisolvens, Anaerocellum thermophilum, Halocella cellulolytica, Thermoanaerobacterium thermosaccharolyticum, Sacharophagus degradans,* or *Thermoanaerobacterium saccharolyticum*. In still another embodiment, the microorganism is genetically modified to enhance activity of one or more hydrolytic enzymes, such as a genetically-modified *Saccaromyces cerevisae*.

In one embodiment, a wild type or a genetically-improved microorganism can be used for chemical production by fermentation. Methods to produce a genetically-improved strain can include genetic modification, mutagenesis, and adaptive processes, such as directed evolution. For example, yeasts can be genetically-modified to ferment C5 sugars. Other useful yeasts are species of *Candida, Cryptococcus, Debaryomyces, Deddera, Hanseniaspora, Kluyveromyces, Pichia, Schizosaccharomyces,* and *Zygosaccharomyces. Rhodococus* strains, such as *Rhodococcus opacus* variants are a source of triacylglycerols and other storage lipids. (See, e.g., Walternann, et al., Microbiology 146:1143-1149 (2000)). Other useful organisms for fermentation include, but are not limited to, yeasts, especially *Saccaromyces* strains and bacteria such as *Clostridium phytofermentans, Thermoanaerobacter ethanolicus, Clostridium thermocellum, Clostridium beijerinickii, Clostridium acetobutylicum, Clostridium tyrobutyricum, Clostridium thermobutyricum, Thermoanaerobacterium saccharolyticum, Thermoanaerobacter thermohydrosulfuricus, Clostridium acetobutylicum, Moorella* ssp., *Carboxydocella* ssp., *Zymomonas mobilis,* recombinant *E. Coli, Klebsiella oxytoca, Rhodococcus opacus* and *Clostridium beijerickii*.

An advantage of yeasts are their ability to grow under conditions that include elevated ethanol concentration, high sugar concentration, low sugar concentration, and/or operate under anaerobic conditions. These characteristics, in various combinations, can be used to achieve operation with long or short fermentation cycles and can be used in combination with batch fermentations, fed batch fermentations, self-seeding/partial harvest fermentations, and recycle of cells from the final fermentation as inoculum.

Examples of yeasts that can be used as a biocatalyst or fermentive microorganism in the methods disclosed herein include but are not limited to, species found in the genus *Ascoidea, Brettanomyces, Candida, Cephaloascus, Coccidiascus, Dipodascus, Eremothecium, Galactomyces, Kluyveromyces, Pichia, Saccharomyces, Schizosaccharomyces, Sporopachydermia, Torulaspora, Yarrowia,* or *Zygosaccharomyces*; for example, *Ascoidea rebescens, Brettanomyces anomalus, Brettanomyces bruxellensis, Brettanomyces claussenii, Brettanomyces custersianus, Brettanomyces lambicus, Brettanomyces naardenensis, Brettanomyces nanus, Candida albicans, Candida ascalaphidarum, Candida amphixiae, Candida antarctica, Candida argentea, Candida atlantica, Candida atmosphaerica, Candida blattae, Candida carpophila, Candida cerambycidarum, Candida chauliodes, Candida corydali, Candida dosseyi, Candida dubliniensis, Candida ergatensis, Candida fructus, Candida glabrata, Candida fermentati, Candida guilliermondii, Candida haemulonii, Candida insectamens, Candida insectorum, Candida intermedia, Candida jeffresii, Candida kefyr, Candida krusei, Candida lusitaniae, Candida lyxosophila, Candida maltosa, Candida marina, Candida membranifaciens, Candida milleri, Candida oleophila, Candida oregonensis, Candida parapsilosis, Candida quercitrusa, Candida rugosa, Candida sake, Candida shehatea, Candida temnochilae, Candida tenuis, Candida tropicalis, Candida tsuchiyae, Candida sinolaborantium, Candida sojae, Candida subhashii, Candida viswanathii, Candida utilis, Cephaloascus fragrans, Coccidiascus legeri, Dypodascus albidus, Eremothecium cymbalariae, Galactomyces candidum, Galactomyces geotrichum, Kluyveromyces aestuarii, Kluyveromyces africanus, Kluyveromyces bacillisponus, Kluyveromyces blattae, Kluyveromyces dobzhanskii, Kluyveromyces hubeiensis, Kluyveromyces lactis, Kluyveromyces lodderae, Kluyveromyces marxianus, Kluyveromyces nonfermentans, Kluyveromyces piceae, Kluyveromyces sinensis, Kluyveromyces thermotolerans, Kluyveromyces waltii, Kluyveromyces wickerhamii, Kluyveromyces yarrowii, Pichia anomola, Pichia heedii, Pichia guilliermondii, Pichia kluyveri, Pichia membranifaciens, Pichia nonvegensis, Pichia ohmeri, Pichia pastoris, Pichia subpelliculosa, Saccharomyces bayanus, Saccharomyces boulardii, Saccharomyces bulderi, Saccharomyces cariocanus, Saccharomyces cariocus, Saccharomyces cerevisiae, Saccharomyces chevalieri, Saccharomyces dairenensis, Saccharomyces ellipsoideus, Saccharomyces eubayanus, Saccharomyces exiguus, Saccharomyces florentinus, Saccharomyces kluyveri, Saccharomyces martiniae, Saccharomyces monacensis, Saccharomyces norbensis, Saccharomyces paradoxus, Saccharomyces pastorianus, Saccharomyces spencerorum, Saccharomyces turicensis, Saccharomyces unisporus, Saccharomyces uvanum, Saccharomyces zonatus, Schizosaccharomyces cryophilus, Schizosaccharomyces japonicus, Schizosaccharomyces octosponus, Schizosaccharomyces pombe, Sporopachydermia cereana, Sporopachydermia lactativora, Sporopachydermia quercuum, Torulaspora delbnueckii, Torulaspora franciscae, Torulaspora globosa, Torulaspora pretoriensis, Yarrowia lipolytica, Zygosaccharomyces bailii, Zygosaccharomyces bisponus, Zygosaccharomyces cidri, Zygosaccharomyces fermentati, Zygosaccharomyces florentinus, Zygosaccharomyces kombuchaensis, Zygosaccharomyces lentus, Zygosaccharomyces mellis, Zygosaccharomyces microellipsoides, Zygosaccharomyces mrakii, Zygosaccharomyces pseudorouxii,* or *Zygosaccharomyces rouxii,* or a variant or genetically modified version thereof.

Examples of bacteria that can be used as a biocatalyst or fermentive microorganism in the methods disclosed herein include but are not limited to any bacterium found in the genus of *Butyrivibrio, Ruminococcus, Eubacterium, Bacteroides, Acetivibrio, Caldibacillus, Acidothermus, Cellulomonas, Curtobacterium, Micromonospora, Actinoplanes, Streptomyces, Thermobifida, Thermomonospora, Microbispora, Fibrobacter, Sporocytophaga, Cytophaga, Flavobacterium, Achromobacter, Xanthomonas, Cellvibrio, Pseudomonas, Myxobacter, Escherichia, Klebsiella, Thermoanaerobacterium, Thermoanaerobacter, Geobacillus, Saccharococcus, Paenibacillus, Bacillus, Caldicellulosiruptor, Anaerocellum, Anoxybacillus, Zymomonas, Clostridium*; for example, *Butyrivibrio fibrisolvens, Ruminococcus flavefaciens, Ruminococcus succinogenes, Ruminococcus albus, Eubacterium cellulolyticum, Bacteroides cellulosolvens, Acetivibrio cellulolyticus, Acetivibrio cellulosolvens, Caldibacillus cellulovorans, Bacillus circulans, Acidothermus cellulolyticus, Cellulomonas cartae, Cellulomonas cellasea, Cellulomonas cellulans, Cellulomonas fimi, Cellulomonas flavigena, Cellulomonas gelida, Cellulomonas iranensis, Cellulomonas persica, Cellulomonas uda, Curtobacterium falcumfaciens, Micromonospora melonosporea, Actinoplanes aurantiaca, Streptomyces reticuli, Streptomyces*

*alboguseolus, Streptomyces aureofaciens, Streptomyces cellulolyticus, Streptomyces flavogriseus, Streptomyces lividans, Streptomyces nitrosporeus, Streptomyces olivochromogenes, Streptomyces rochei, Streptomyces thermovulgaris, Streptomyces viridosporus, Thermobifida alba, Thermobifida fusca, Thermobifida cellulolytica, Thermomonospora curvata, Microbispora bispora, Fibrobacter succinogenes, Sporocytophaga myxococcoides, Cytophaga sp., Flavobacterium johnsoniae, Achromobacter piechaudii, Xanthomonas sp., Cellvibrio vulgaris, Cellvibrio fulvus, Cellvibrio gilvus, Cellvibrio mixtus, Pseudomonas fluorescens, Pseudomonas mendocina, Myxobacter sp. AL-1, Escherichia albertii, Escherichia blattae, Escherichia coli, Escherichia fergusonii, Escherichia hermannii, Escherichia vulneris, Klebsiella granulomatis, Klebsiella oxytoca, Klebsiella pneumonia, Klebsiella terrigena, Thermoanaerobacterium thermosulfurigenes, Thermoanaerobacterium aotearoense, Thermoanaerobacterium polysaccharolyticum, Thermoanaerobacterium zeae, Thermoanaerobacterium xylanolyticum, Thermoanaerobacterium saccharolyticum, Thermoanaerobium brockii, Thermoanaerobacterium thermosaccharolyticum, Thermoanaerobacter thermohydrosulfuricus, Thermoanaerobacter ethanolicus, Thermoanaerobacter brocki, Geobacillus thermoglucosidasius, Geobacillus stearothermophilus, Saccharococcus caldoxylosilyticus, Saccharoccus thermophilus, Paenibacillus campinasensis, Bacillus flavothermus, Anoxybacillus kamchatkensis, Anoxybacillus gonensis, Caldicellulosiruptor acetigenus, Caldicellulosiruptor saccharolyticus, Caldicellulosiruptor kristjanssonii, Caldicellulosiruptor owensensis, Caldicellulosiruptor lactoaceticus, Anaerocellum thermophilum, Clostridium thermocellum, Clostridium cellulolyticum, Clostridium straminosolvens, Clostridium acetobutylicum, Clostridium aerotolerans, Clostridium beijerinckii, Clostridium bifermentans, Clostridium botulinum, Clostridium butyricum, Clostridium cadaveric, Clostridium chauvoei, Clostridium clostridioforme, Clostridium colicanis, Clostridium difficile, Clostridium fallax, Clostridium formicaceticum, Clostridium histolyticum, Clostridium innocuum, Clostridium ljungdahlii, Clostridium laramie, Clostridium lavalense, Clostridium novyi, Clostridium oedematiens, Clostridium paraputrificum, Clostridium perfringens, Clostridium phytofermentans, Clostridium piliforme, Clostridium ramosum, Clostridium scatologenes, Clostridium septicum, Clostridium sordellii, Clostridium sporogenes, Clostridium tertium, Clostridium tetani, Clostridium tyrobutyricum, Clostridium thermobutyricum, Zymomonas mobilis*, or a variant or genetically modified version thereof.

In one embodiment, fed-batch fermentation is performed on the treated biomass to produce a fermentation end-product, such as alcohol, ethanol, organic acid, succinic acid, TAG, or hydrogen. In one embodiment, the fermentation process comprises simultaneous hydrolysis and fermentation (SSF) of the biomass using one or more microorganisms such as a *Rhodococcus* strain, a *Clostridium* strain, a *Trichoderma* strain, a *Saccharomyces* strain, a *Zymomonas* strain, or another microorganism suitable for fermentation of biomass. In another embodiment, the fermentation process comprises simultaneous hydrolysis and fermentation of the biomass using a microorganism that is *Clostridium algidixylanolyticum, Clostridium xylanolyticum, Clostridium cellulovorans, Clostridium cellulolyticum, Clostridium thermocellum, Clostridium josui, Clostridium papyrosolvens, Clostridium cellobioparum, Clostridium hungatei, Clostridium cellulosi, Clostridium stercorarium, Clostridium termitidis, Clostridium thermocopriae, Clostridium celerecrescens, Clostridium polysaccharolyticum, Clostridium populeti, Clostridium lentocellum, Clostridium chartatabidum, Clostridium aldrichii, Clostridium herbivorans, Clostridium phytofermentans, Acetivibrio cellulolyticus, Bacteroides cellulosolvens, Caldicellulosiruptor saccharolyticum, Ruminococcus albus, Ruminococcus flavefaciens, Fibrobacter succinogenes, Eubacterium cellulosolvens, Butyrivibrio fibrisolvens, Anaerocellum thermophilum, Halocella cellulolytica, Thermoanaerobacterium thermosaccharolyticum, Sacharophagus degradans*, or *Thermoanaerobacterium saccharolyticum*.

In one embodiment, the fermentation process can include separate hydrolysis and fermentation (SHF) of a biomass with one or more enzymes, such as a xylanases, endo-1,4-beta-xylanases, xylosidases, beta-D-xylosidases, cellulases, hemicellulases, carbohydrases, glucanases, endoglucanases, endo-1,4-beta-glucanases, exoglucanases, glucosidases, beta-D-glucosidases, amylases, cellobiohydrolases, exocellobiohydrolases, phytases, proteases, peroxidase, pectate lyases, galacturonases, or laccases. In one embodiment, one or more enzymes used to treat a biomass is thermostable. In another embodiment, a biomass is treated with one or more enzymes, such as those provided herein, prior to fermentation. In another embodiment, a biomass is treated with one or more enzymes, such as those provided herein, during fermentation. In another embodiment, a biomass is treated with one or more enzymes, such as those provided herein, prior to fermentation and during fermentation. In another embodiment, an enzyme used for hydrolysis of a biomass is the same as those added during fermentation. In another embodiment, an enzyme used for hydrolysis of biomass is different from those added during fermentation.

In some embodiments, fermentation can be performed in an apparatus such as bioreactor, a fermentation vessel, a stirred tank reactor, or a fluidized bed reactor. In one embodiment, the treated biomass can be supplemented with suitable chemicals to facilitate robust growth of the one or more fermenting organisms. In one embodiment, a useful supplement includes but is not limited to, a source of nitrogen and/or amino acids such as yeast extract, cysteine, or ammonium salts (e.g. nitrate, sulfate, phosphate etc.); a source of simple carbohydrates such as corn steep liquor, and malt syrup; a source of vitamins such as yeast extract; buffering agents such as salts (including but not limited to citrate salts, phosphate salts, or carbonate salts); or mineral nutrients such as salts of magnesium, calcium, or iron. In some embodiments redox modifiers are added to the fermentation mixture including but not limited to cysteine or mercaptoethanol.

In one embodiment, the titer and/or productivity of fermentation end-product production by a microorganism is improved by culturing the microorganism in a medium comprising one or more compounds comprising hexose and/or pentose sugars. In one embodiment, a process comprises conversion of a starting material (such as a biomass) to a biofuel, such as one or more alcohols. In one embodiment, methods can comprise contacting substrate comprising both hexose (e.g. glucose, cellobiose) and pentose (e.g. xylose, arabinose) saccharides with a microorganism that can hydrolyze C5 and C6 saccharides to produce ethanol. In another embodiment, methods can comprise contacting substrate comprising both hexose (e.g. glucose, cellobiose) and pentose (e.g. xylose, arabinose) saccharides with *R. opacus* to produce TAG.

In some embodiments, batch fermentation with a microorganism of a mixture of hexose and pentose saccharides using the methods disclosed herein can provide uptake rates of about 0.1-8 g/L/h or more of hexose and about 0.1-8 g/L/h or more of pentose (xylose, arabinose, etc.). In some embodiments, batch fermentation with a microorganism of a mixture of hexose and pentose saccharides using the methods disclosed herein can provide uptake rates of about 0.1, 0.2, 0.4, 0.5, 0.6 0.7, 0.8, 1, 2, 3, 4, 5, or 6 g/L/h or more of hexose and about 0.1, 0.2, 0.4, 0.5, 0.6 0.7, 0.8, 1, 2, 3, 4, 5, or 6 g/L/h or more of pentose.

In one embodiment, a method for production of ethanol or another alcohol produces about 10 g/l to 120 gain 40 hours or less. In another embodiment, a method for production of ethanol produces about 10 g/l, 11 g/L, 12 g/L, 13 g/L, 14 g/L, 15 g/L, 16 g/L, 17 g/L, 18 g/L, 19 g/L, 20 g/L, 21 g/L, 22 g/L, 23 g/L, 24 g/L, 25 g/L, 26 g/L, 27 g/L, 28 g/L, 29 g/L, 30 g/L, 31 g/L, 32 g/L, 33 g/L, 34 g/L, 35 g/L, 36 g/L, 37 g/L, 38 g/L, 39 g/L, 40 g/L, 41 g/L, 42 g/L, 43 g/L, 44 g/L, 45 g/L, 46 g/L, 47 g/L, 48 g/L, 49 g/L, 50 g/L, 51 g/L, 52 g/L, 53 g/L, 54 g/L, 55 g/L, 56 g/L, 57 g/L, 58 g/L, 59 g/L, 60 g/L, 61 g/L, 62 g/L, 63 g/L, 64 g/L, 65 g/L, 66 g/L, 67 g/L, 68 g/L, 69 g/L, 70 g/L, 71 g/L, 72 g/L, 73 g/L, 74 g/L, 75 g/L, 76 g/L, 77 g/L, 78 g/L, 79 g/L, 80 g/L, 81 g/L, 82 g/L, 83 g/L, 84 g/L, 85 g/L, 86 g/L, 87 g/L, 88 g/L, 89 g/L, 90 g/L, 91 g/L, 92 g/L, 93 g/L, 94 g/L, 95 g/L, 96 g/L, 97 g/L, 98 g/L, 99 g/L, 100 g/L, 110 g/l, 120 g/l, or more alcohol in 40 hours by the fermentation of biomass. In another embodiment, alcohol is produced by a method comprising simultaneous fermentation of hexose and pentose saccharides. In another embodiment, alcohol is produced by a microorganism comprising simultaneous fermentation of hexose and pentose saccharides.

In another embodiment, the level of a medium component is maintained at a desired level by adding additional medium component as the component is consumed or taken up by the organism. Examples of medium components included, but are not limited to, carbon substrate, nitrogen substrate, vitamins, minerals, growth factors, cofactors, and biocatalysts. The medium component can be added continuously or at regular or irregular intervals. In one embodiment, additional medium component is added prior to the complete depletion of the medium component in the medium. In one embodiment, complete depletion can effectively be used, for example to initiate different metabolic pathways, to simplify downstream operations, or for other reasons as well. In one embodiment, the medium component level is allowed to vary by about 10% around a midpoint, in one embodiment, it is allowed to vary by about 30% around a midpoint, and in one embodiment, it is allowed to vary by 60% or more around a midpoint. In one embodiment, the medium component level is maintained by allowing the medium component to be depleted to an appropriate level, followed by increasing the medium component level to another appropriate level. In one embodiment, a medium component, such as vitamin, is added at two different time points during fermentation process. For example, one-half of a total amount of vitamin is added at the beginning of fermentation and the other half is added at midpoint of fermentation.

In another embodiment, the nitrogen level is maintained at a desired level by adding additional nitrogen-containing material as nitrogen is consumed or taken up by the organism. The nitrogen-containing material can be added continuously or at regular or irregular intervals. Useful nitrogen levels include levels of about 5 to about 10 g/L. In one embodiment, levels of about 1 to about 12 g/L can also be usefully employed. In another embodiment, levels, such as about 0.5, 0.1 g/L or even lower, and higher levels, such as about 20, 30 g/L or even higher are used. In another embodiment, a useful nitrogen level is about 0.01, 0.05, 0.1, 0.2, 0.3, 0.4, 0.5, 0.6, 0.7, 0.8, 0.9, 1, 2, 3, 4, 5, 6, 7, 8, 9, 10, 11, 12, 13, 14, 15, 16, 17, 18, 19, 20, 21, 22 23, 24, 25, 26, 27, 28, 29 or 30 g/L. Nitrogen can be supplied as a simple nitrogen-containing material, such as an ammonium compounds (e.g. ammonium sulfate, ammonium hydroxide, ammonia, ammonium nitrate, or any other compound or mixture containing an ammonium moiety), nitrate or nitrite compounds (e.g. potassium, sodium, ammonium, calcium, or other compound or mixture containing a nitrate or nitrite moiety), or as a more complex nitrogen-containing material, such as amino acids, proteins, hydrolyzed protein, hydrolyzed yeast, yeast extract, dried brewer's yeast, yeast hydrolysates, distillers' grains, soy protein, hydrolyzed soy protein, fermentation products, and processed or corn steep powder or unprocessed protein-rich vegetable or animal matter, including those derived from bean, seeds, soy, legumes, nuts, milk, pig, cattle, mammal, fish, as well as other parts of plants and other types of animals. Nitrogen-containing materials useful in various embodiments also include materials that contain a nitrogen-containing material, including, but not limited to mixtures of a simple or more complex nitrogen-containing material mixed with a carbon source, another nitrogen-containing material, or other nutrients or non-nutrients, and AFEX treated plant matter.

In another embodiment, the carbon level is maintained at a desired level by adding sugar compounds or material containing sugar compounds ("Sugar-Containing Material") as sugar is consumed or taken up by the organism. The sugar-containing material can be added continuously or at regular or irregular intervals. In one embodiment, additional sugar-containing material is added prior to the complete depletion of the sugar compounds available in the medium. In one embodiment, complete depletion can effectively be used, for example to initiate different metabolic pathways, to simplify downstream operations, or for other reasons as well. In one embodiment, the carbon level (as measured by the grams of sugar present in the sugar-containing material per liter of broth) is allowed to vary by about 10% around a midpoint, in one embodiment, it is allowed to vary by about 30% around a midpoint, and in one embodiment, it is allowed to vary by 60% or more around a midpoint. In one embodiment, the carbon level is maintained by allowing the carbon to be depleted to an appropriate level, followed by increasing the carbon level to another appropriate level. In some embodiments, the carbon level can be maintained at a level of about 5 to about 120 g/L. However, levels of about 30 to about 100 g/L can also be usefully employed as well as levels of about 60 to about 80 g/L. In one embodiment, the carbon level is maintained at greater than 25 g/L for a portion of the culturing. In another embodiment, the carbon level is maintained at about 5 g/L, 6 g/L, 7 g/L, 8 g/L, 9 g/L, 10 g/L, 11 g/L, 12 g/L, 13 g/L, 14 g/L, 15 g/L, 16 g/L, 17 g/L, 18 g/L, 19 g/L, 20 g/L, 21 g/L, 22 g/L, 23 g/L, 24 g/L, 25 g/L, 26 g/L, 27 g/L, 28 g/L, 29 g/L, 30 g/L, 31 g/L, 32 g/L, 33 g/L, 34 g/L, 35 g/L, 36 g/L, 37 g/L, 38 g/L, 39 g/L, 40 g/L, 41 g/L, 42 g/L, 43 g/L, 44 g/L, 45 g/L, 46 g/L, 47 g/L, 48 g/L, 49 g/L, 50 g/L, 51 g/L, 52 g/L, 53 g/L, 54 g/L, 55 g/L, 56 g/L, 57 g/L, 58 g/L, 59 g/L, 60 g/L, 61 g/L, 62 g/L, 63 g/L, 64 g/L, 65 g/L, 66 g/L, 67 g/L, 68 g/L, 69 g/L, 70 g/L, 71 g/L, 72 g/L, 73 g/L, 74 g/L, 75 g/L, 76 g/L, 77 g/L, 78 g/L, 79 g/L, 80 g/L, 81 g/L, 82 g/L, 83 g/L, 84 g/L, 85 g/L, 86 g/L, 87 g/L, 88 g/L, 89 g/L, 90 g/L, 91 g/L, 92 g/L, 93 g/L, 94 g/L, 95 g/L, 96 g/L, 97 g/L, 98 g/L, 99 g/L, 100 g/L, 101 g/L, 102 g/L, 103 g/L, 104 g/L, 105 g/L, 106 g/L, 107 g/L, 108 g/L, 109 g/L, 110 g/L, 111 g/L, 112 g/L, 113 g/L, 114 g/L, 115 g/L, 116 g/L, 117 g/L, 118 g/L, 119 g/L, 120 g/L, 121 g/L, 122 g/L, 123 g/L, 124 g/L, 125 g/L, 126 g/L, 127 g/L, 128 g/L, 129 g/L, 130 g/L, 131 g/L, 132 g/L, 133 g/L, 134 g/L, 135 g/L, 136 g/L, 137 g/L, 138 g/L, 139 g/L, 140 g/L, 141 g/L, 142 g/L, 143 g/L, 144 g/L, 145 g/L, 146 g/L, 147 g/L, 148 g/L, 149 g/L, or 150 g/L.

The carbon substrate, like the nitrogen substrate, can be used for cell production and enzyme production, but unlike the nitrogen substrate, the carbon substrate can serve as the raw material for production of fermentation end-products. Frequently, more carbon substrate can lead to greater production of fermentation end-products. In another embodiment, it can be advantageous to operate with the carbon level and nitrogen level related to each other for at least a portion of the fermentation time. In one embodiment, the ratio of carbon to nitrogen is maintained within a range of about 30:1 to about 10:1. In another embodiment, the ratio of carbon nitrogen is maintained from about 20:1 to about 10:1 or more preferably from about 15:1 to about 10:1. In another embodiment, the ratio of carbon nitrogen is about 30:1, 29:1, 28:1, 27:1, 26:1, 25:1, 24:1, 23:1, 22:1, 21:1, 20:1, 19:1, 18:1, 17:1, 16:1, 15:1, 14:1, 13:1, 12:1, 11:1, 10:1, 9:1, 8:1, 7:1, 6:1, 5:1, 4:1, 3:1, 2:1, or 1:1.

Maintaining the ratio of carbon and nitrogen ratio within particular ranges can result in benefits to the operation such as the rate of metabolism of carbon substrate, which depends on the amount of carbon substrate and the amount and activity of enzymes present, being balanced to the rate of end product production. Balancing the carbon to nitrogen ratio can, for example, facilitate the sustained production of these enzymes such as to replace those which have lost activity.

In another embodiment, the amount and/or timing of carbon, nitrogen, or other medium component addition can be related to measurements taken during the fermentation. For example, the amount of monosaccharides present, the amount of insoluble polysaccharide present, the polysaccharase activity, the amount of product present, the amount of cellular material (for example, packed cell volume, dry cell weight, etc.) and/or the amount of nitrogen (for example, nitrate, nitrite, ammonia, urea, proteins, amino acids, etc.) present can be measured. The concentration of the particular species, the total amount of the species present in the fermentor, the number of hours the fermentation has been running, and the volume of the fermentor can be considered. In various embodiments, these measurements can be compared to each other and/or they can be compared to previous measurements of the same parameter previously taken from the same fermentation or another fermentation. Adjustments to the amount of a medium component can be accomplished such as by changing the flow rate of a stream containing that component or by changing the frequency of the additions for that component. For example, the amount of saccharide can be increased when the cell production increases faster than the end product production. In another embodiment, the amount of nitrogen can be increased when the enzyme activity level decreases.

In another embodiment, a fed batch operation can be employed, wherein medium components and/or fresh cells are added during the fermentation without removal of a portion of the broth for harvest prior to the end of the fermentation. In one embodiment, a fed-batch process is based on feeding a growth limiting nutrient medium to a culture of microorganisms. In one embodiment, the feed medium is highly concentrated to avoid dilution of the bioreactor. In another embodiment, the controlled addition of the nutrient directly affects the growth rate of the culture and avoids overflow metabolism such as the formation of side metabolites. In one embodiment, the growth limiting nutrient is a nitrogen source or a saccharide source.

In various embodiments, particular medium components can have beneficial effects on the performance of the fermentation, such as increasing the titer of desired products, or increasing the rate that the desired products are produced. Specific compounds can be supplied as a specific, pure ingredient, such as a particular amino acid, or it can be supplied as a component of a more complex ingredient, such as using a microbial, plant or animal product as a medium ingredient to provide a particular amino acid, promoter, cofactor, or other beneficial compound. In some cases, the particular compound supplied in the medium ingredient can be combined with other compounds by the organism resulting in a fermentation-beneficial compound. One example of this situation would be where a medium ingredient provides a specific amino acid which the organism uses to make an enzyme beneficial to the fermentation. Other examples can include medium components that are used to generate growth or product promoters, etc. In such cases, it can be possible to obtain a fermentation-beneficial result by supplementing the enzyme, promoter, growth factor, etc. or by adding the precursor. In some situations, the specific mechanism whereby the medium component benefits the fermentation is not known, only that a beneficial result is achieved.

In one embodiment, a fermentation to produce a fuel is performed by culturing a strain of R. opacus in a medium having a supplement of lignin component and a concentration of one or more carbon sources. The resulting production of end product such as TAG can be up to 1-fold, 2-fold, 3-fold, 4-fold, 5-fold, 6-fold, 7-fold, 8-fold, 9-fold, and in some cases up to 10-fold and higher in volumetric productivity than a process using only the addition of a relatively pure saccharide source, and can achieve a carbon conversion efficiency approaching the theoretical maximum. The theoretical maximum can vary with the substrate and product. For example, the generally accepted maximum efficiency for conversion of glucose to ethanol is 0.51 g ethanol/g glucose. In one embodiment, a biocatalyst can produce about 40-100% of a theoretical maximum yield of ethanol. In another embodiment, a biocatalyst can produce up to about 40%, 50%, 60%, 70%, 80%, 90%, 95% and even 100% of the theoretical maximum yield of ethanol. In one embodiment, a biocatalyst can produce up to about 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, 99.99%, or 100% of a theoretical maximum yield of a fuel. It can be possible to obtain a fermentation-beneficial result by supplementing the medium with a pretreatment or hydrolysis component. In some situations, the specific mechanism whereby the medium component benefits the fermentation is not known, only that a beneficial result is achieved.

Various embodiments offer benefits relating to improving the titer and/or productivity of fermentation end-product production by a biocatalyst by culturing the organism in a medium comprising one or more compounds comprising particular fatty acid moieties and/or culturing the organism under conditions of controlled pH.

In one embodiment, the pH of the medium is controlled at less than about pH 7.2 for at least a portion of the fermentation. In one embodiment, the pH is controlled within a range of about pH 3.0 to about 7.1 or about pH 4.5 to about 7.1, or about pH 5.0 to about 6.3, or about pH 5.5 to about 6.3, or about pH 6.0 to about 6.5, or about pH 5.5 to about 6.9 or about pH 6.2 to about 6.7. The pH can be controlled by the addition of a pH modifier. In one embodiment, a pH modifier is an acid, a base, a buffer, or a material that reacts with other materials present to serve to raise of lower the pH. In one embodiment, more than one pH modifier can be used, such as more than one acid, more than one base, one or more acid with one or more bases, one or more acids with one or more buffers, one or more bases with one or more buffers, or one or more acids with one or more bases with one or more buffers. When more than one pH modifiers are utilized, they can be added at the same time or at different times. In one embodiment, one or more acids and one or more bases can be combined, resulting in a buffer. In one embodiment, media components, such as a carbon source or a nitrogen source can also serve as a pH modifier; suitable media components include those with high or low pH or those with buffering capacity. Exemplary media components include acid- or base-hydrolyzed plant polysaccharides having with residual acid or base, AFEX treated plant material with residual ammonia, lactic acid, corn steep solids or liquor.

In one embodiment, a constant pH can be utilized throughout the fermentation. In one embodiment, the timing and/or amount of pH reduction can be related to the growth conditions of the cells, such as in relation to the cell count, the end product produced, the end product present, or the rate of end product production. In one embodiment, the pH reduction can be made in relation to physical or chemical properties of the fermentation, such as viscosity, medium composition, gas production, off gas composition, etc.

Recovery of Fermentation End Products

In another aspect, methods are provided for the recovery of the fermentive end products, such as an alcohol (e.g. ethanol, propanol, methanol, butanol, etc.) another biofuel or chemical product. In one embodiment, broth will be harvested at some point during of the fermentation, and fermentive end product or products will be recovered. The broth with end product to be recovered will include both end product and impurities. The impurities include materials such as water, cell bodies, cellular debris, excess carbon substrate, excess nitrogen substrate, other remaining nutrients, other metabolites, and other medium components or digested medium components. During the course of processing the broth, the broth can be heated and/or reacted with various reagents, resulting in additional impurities in the broth.

In one embodiment, the processing steps to recover end product frequently includes several separation steps, including, for example, distillation of a high concentration alcohol material from a less pure alcohol-containing material. In one embodiment, the high concentration alcohol material can be further concentrated to achieve very high concentration alcohol, such as 98% or 99% or 99.5% (wt.) or even higher. Other separation steps, such as filtration, centrifugation, extraction, adsorption, etc. can also be a part of some recovery processes for alcohol as a product or biofuel, or other biofuels or chemical products.

In one embodiment, a process can be scaled to produce commercially useful biofuels. In another embodiment, biocatalyst is used to produce an alcohol, e.g., ethanol, butanol, propanol, methanol, or a fuel such as hydrocarbons hydrogen, TAG, and hydroxy compounds. In another embodiment, biocatalyst is used to produce a carbonyl compound such as an aldehyde or ketone (e.g. acetone, formaldehyde, 1-propanal, etc.), an organic acid, a derivative of an organic acid such as an ester (e.g. wax ester, glyceride, etc.), 1,2-propanediol, 1,3-propanediol, lactic acid, formic acid, acetic acid, succinic acid, pyruvic acid, or an enzyme such as a cellulase, polysaccharase, lipases, protease, ligninase, and hemicellulase.

TAG biosynthesis is widely distributed in nature and the occurrence of TAG as reserve compounds is widespread among plants, animals, yeast and fungi. In contrast, however, TAGs have not been regarded as common storage compounds in bacteria. Biosynthesis and accumulation of TAGs have been described only for a few bacteria belonging to the actinomycetes group, such as genera of *Streptomyces, Nocardia, Rhodococcus, Mycobacterium, Dietzia* and *Gordonia*, and, to a minor extent, also in a few other bacteria, such as *Acinetobacter baylyi* and *Alcanivorax borkumensis*. Since the mid-1990's, TAG production in hydrocarbon-degrading strains of those genera has been frequently reported. TAGs are stored in spherical lipid bodies as intracellular inclusions, with the amounts depending on the respective species, cultural conditions and growth phase. Commonly, the important factor for the production of TAGs is the amount of nitrogen that is supplied to the culture medium. The excess carbon, which is available to the culture after nitrogen exhaustion, continues to be assimilated by the cells and, by virtue of oleaginous bacteria possessing the requisite enzymes, is converted directly into lipid. The compositions and structures of bacterial TAG molecules vary considerably depending on the bacterium and on the cultural conditions, especially the carbon sources. See, Brigham C J, et al. (2011) J Microbial Biochem Technol S3:002.

In one embodiment, useful biochemicals can be produced from non-food plant biomass, with a steam or hot-water extraction technique that is carried out by contacting a charge of non-food plant pretreated biomass material such as corn stover or sorghum with water and/or acid (with or without additional process enhancing compounds or materials), in a pressurized vessel at an elevated temperature up to about 160-220° C. and at a pH below about 7.0, to yield an aqueous (extract solution) mixture of useful sugars including long-chain saccharides (sugars), acetic acid, and lignin, while leaving the structural (cellulose and lignin) portion of the lignocellulosic material largely intact. In combination, these potential inhibitory chemicals especially sugar degradation products are low, and the plant derived nutrients that are naturally occurring lignocellulosic-based components are also recovered that are beneficial to a C5 and C6 fermenting organism. Toward this objective, the aqueous extract is concentrated (by centrifugation, filtration, solvent extraction, flocculation, evaporation), by producing a concentrated sugar stream, apart from the other hemicellulose (C5 rich) and cellulosic derived sugars (C6 rich) which are channeled into a fermentable stream.

In another embodiment, following enzyme/acid hydrolysis, additional chemical compounds that are released are recovered with the sugar stream resulting in a short-chain sugar solution containing xylose, mannose, arabinose, rhamnose, galactose, and glucose (5 and 6-carbon sugars). The sugar stream, now significantly rich in C5 and C6 substances can be converted by microbial fermentation or chemical catalysis into such products as triacylglycerol or TAG and further refined to produce stream rich in JP8 or jet fuels. If C5 sugar percentage correction has not been performed, it can be performed before fermentation to satisfy desired combination of C5 and C6 sugars for the fermentation organism and corresponding end product.

Figure 4:
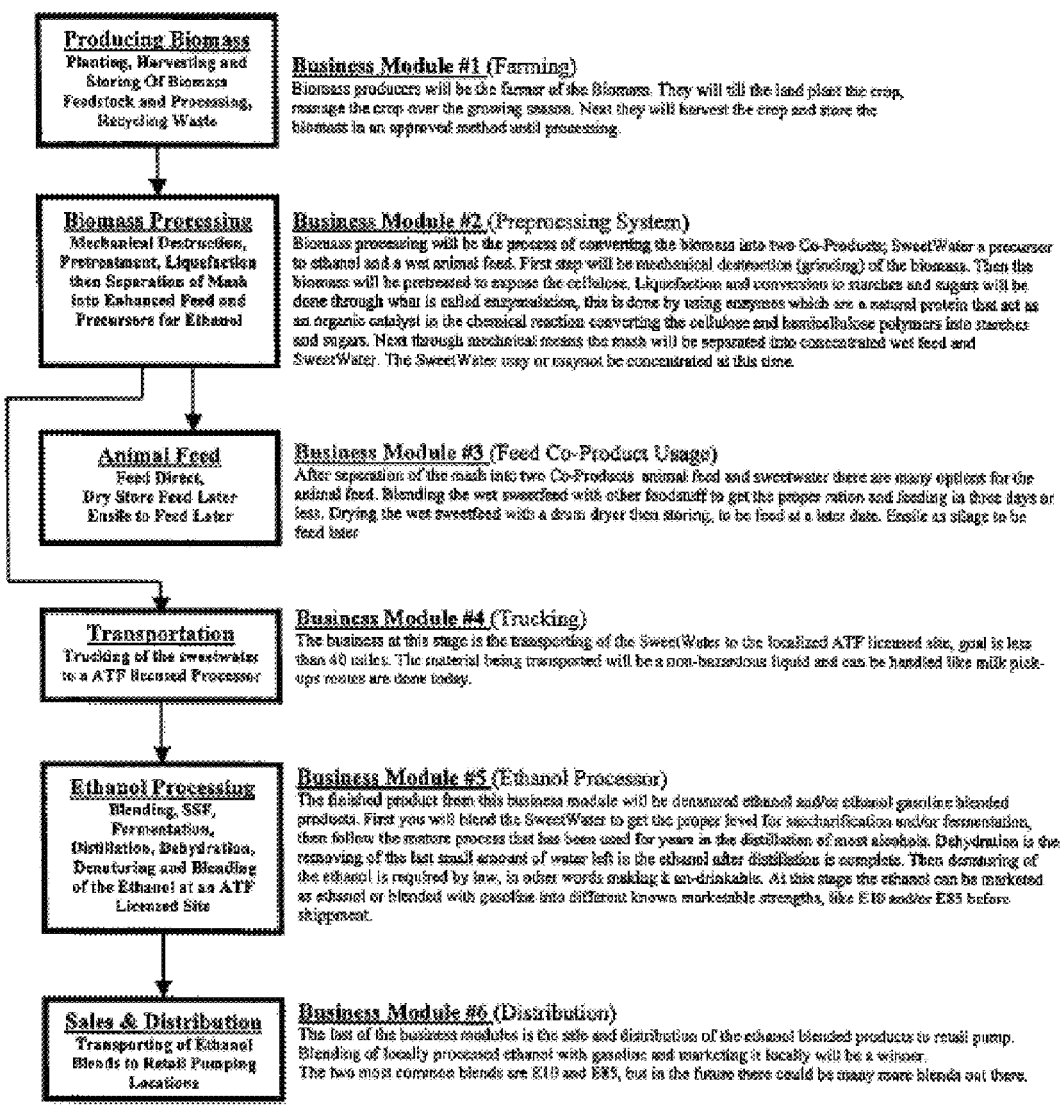
FIG. 4 is a schematic illustration outlining the steps and elements of the preferred method and system of the present invention.
Figure 5:
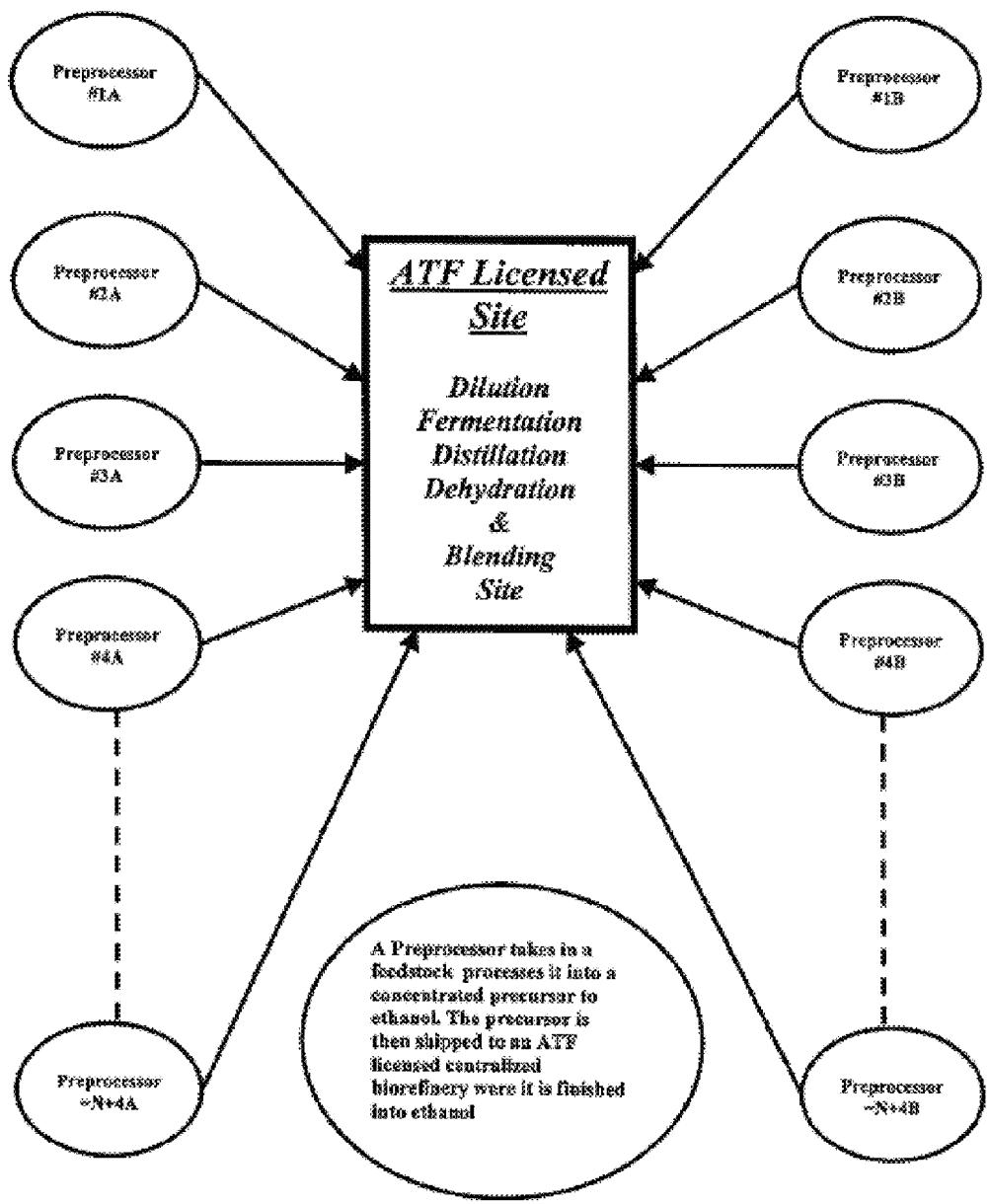
FIG. 5 is a schematic illustration of the plurality of feedstock processing plants and the ethanol producing plant of the preferred method and system of the present invention.

An embodiment of the method and system in accordance with the present invention is illustrated in FIGS. 4 through 5. As shown in FIG. 4, the first step of the method for producing ethanol is providing feedstock. Feedstock providers include farmers who plant, manage and harvest crops such as corn. Feedstock providers may also include feedstock storage facilities, food processors, recycle centers and other feedstock providing sites. Feedstock providers may also include those who specifically produce feedstock for the sole purpose of producing ethanol. The feedstock provided may include hard grains, cellulose biomasses, waste materials, biomasses farmed for the sole purpose of producing ethanol, old and/or poor quality animal feed, animal manure and the like. It is contemplated, however, that the feedstock provided may include any material or substance that may be used to produce ethanol. While FIG. 4 describes a method and system for providing feedstock, it is contemplated within the scope of the invention, however, that any suitable method and system for providing feedstock may be used.

Still referring to FIG. 4, the second step of the method and system for producing ethanol is processing the feedstock. The processing of feedstock step is performed at a feedstock providing site. As a result, it is contemplated that the method and system for producing ethanol will include a plurality of feedstock processing plants located at or near feedstock providing sites. The feedstock processing plants are non-fermenting, non-distilling plants that do not require a license to operate from the United States Department of Alcohol Tobacco and Firearms ("ATF"). Further, the feedstock processing plants produce non-hazardous materials that may be transported as such. Still further, the feedstock processing plants may be portable. The portability of the feedstock processing plant contributes to the transportation cost savings provided by the present invention.

Still referring to FIG. 4, the processing step converts the feedstock into two products; namely, sugar water and wet animal feed. The feedstock may be processed in any number of ways including the following: (1) mechanical destruction (grinding) of the feedstock; (2) pretreatment of the feedstock; and (3) enzymolation, enzymolosis or enzymatic hydrolysis of the feedstock. The pretreatment of the feedstock may include dilute-acid thermochemical pretreatment adapted to hydrolyze the feedstock and break down the feedstock into its component sugars, e.g., xylose, etc. The pretreatment of the feedstock may also solubize a portion of the lignin. Processing of the feedstock also includes enzymatic hydrolysis in which enzymes are used to convert cellulosic biomass into fermentable sugars. More particularly, enzymatic hydroloysis is adapted to release the feedstock's sugars, e.g., glucose. The pretreatment is adapted to make the cellulose of the feedstock more accessible to further treatment. In an embodiment of the method and system for producing ethanol, the sugars of the pretreated feedstock are later fermented into fuel ethanol and the residue lignin may be used for catalytic conversion to other products, gasified or combusted to provide heat and power for the plant operation or for sale.

Still referring to FIG. 4, the processing of feedstock step of the method may also include concentrating the precursor/sugar water. The processing of feedstock step of the method and system for producing ethanol described in FIG. 4 reduces the transportation costs associated with the production of ethanol from feedstock as described in more detail below. While FIG. 4 describes a method and system for processing feedstock, it is contemplated within the scope of the invention that any suitable method for processing feedstock may be used.

Referring still to FIG. 4, the third step of the method and system for producing ethanol is separating the precursor/sugar water and wet animal feed. As described in FIG. 4, the wet animal feed has multiple uses. In addition, the separation of the wet animal feed from the precursor/sugar water further reduces the transporation costs associated with the production of ethanol from feedstock as described in more detail below.

Still referring to FIG. 4, the fourth step of the method and system for producing ethanol is transporting the sugar water from the feedstock processing plant or plants to the ethanol producing plant. In an embodiment of the method and system for producing ethanol, the tonnage that is shipped from the feedstock processing plant to the ethanol producing plant is 100% usable material. Any byproducts generated at the feedstock processing plant may be used as animal feed, animal bedding or compost, biofuel, chemicals or they be land applied. Further, in the method and system for producing ethanol, the precursor/sugar water produced by the feedstock processing plant or plants is a nonhazardous material with relatively few transportation restrictions.

As noted above, steps two and three of the method and system for producing ethanol substantially reduce the transportation costs. More particularly, instead of transporting raw, non-processed feedstock from the feedstock providing site, the method and system for producing ethanol requires that only processed feedstock or precursor/sugar water be transported from the feedstock providing site to the ethanol producing plant. As a result, tonnage and costs such as labor, fuel, repair and maintenance are reduced. By way of example, it is estimated that approximately tonnage may be reduced by approximately 66% to 75% using the method and system for producing ethanol. In addition, storage capacity at the ethanol producing plant may be reduced, thereby minimizing or eliminating the adverse environmental impact caused by storage of feedstock. It is estimated that the total transportation costs associated with incoming feedstock and outgoing byproducts or waste materials may be reduced by approximately 80% using the method and system for producing ethanol.

Still referring to FIG. 4, the fifth step of the method and system for producing ethanol is producing ethanol. The finished product may be denatured ethanol or an ethanol and gasoline blend. In an embodiment of the method and system for producing ethanol, ethanol is produced at an ethanol producing plant from sugar water transported from one or more feedstock processing plants. The ethanol producing plant is a centrally-located (relative to a plurality of feedstock processing plants) site which receives concentrated sugar water from feedstock processing plants and blends the sugar water to the proper sugar level for fermentation. Because ethanol is a form of alcohol, any producer must be licensed by the United States Department of Alcohol Tobacco and Firearms ("ATF"). The fermentation process produces what is commonly referred to as beer. More particularly, the fermentation process yields ethanol and carbon dioxide. After the completion of the fermentation step, the beer is then preferably distilled and dehydrated into 200 proof ethanol by removing the remaining amount of water in the liquid. In an embodiment, the final step is called denaturing which is a process for making the liquid unfit for human consumption. The wastewater produced by the process may be used to dilute the concentrated sugar water, thereby avoiding and/or reducing treatment requirements.

Because the feedstock tonnage transported to the ethanol producing plant is reduced during the feedstock processing and separating steps of the method for producing ethanol, the size, land acquisition cost and plant construction cost of the ethanol producing plant may be reduced.

While FIG. 4 illustrates a process performed at the ethanol producing plant, it is contemplated within the scope of the invention that one or more of these processes may be performed at the one or more feedstock processing plants. In such case, it may be necessary to obtain an ATF license for each such feedstock processing plant. In the alternative, one or more of the processes performed in the first three steps of the method and system for producing ethanol may be performed at the ethanol producing plant. Further, while FIG. 4 illustrates a process for converting sugar water into ethanol, it is contemplated within the scope of the invention that any suitable process for converting sugar water into ethanol may be used.

Still referring to FIG. 4, the sixth step of the method and system for producing ethanol is selling and distributing the ethanol or ethanol blended products produced at the ethanol producing plant. In an embodiment of the method and system for producing ethanol, the ethanol and ethanol blended products are sold and distributed to retail liquid fuel pumping locations. It is contemplated within the scope of the invention that ethanol and ethanol blended products may be sold and distributed to any suitable purchaser and/or distributor. At the present time, the two most common ethanol blended products are E1 0 and E85. However, it is contemplated that the embodiments of the method and system for producing ethanol may be used to produce many other different blends in the future. In addition, it is contemplated within the scope of the invention that the method and system for producing ethanol may be used to produce wet cattle feed, dry cattle feed, 190 proof ethanol, 200 proof ethanol, direct injection fuel and liquid carbon dioxide.

As shown in FIG. 5, the method and system for producing ethanol employs a plurality of feedstock processing plants and a centrally-located, ATF-licensed ethanol producing plant. According to an embodiment of the method and system for producing ethanol, feedstock is processed into sugar water at the plurality of feedstock processing plants. Thereafter, the precursor/sugar water is transported to the centrally-located, ATF-licensed ethanol producing plant where it is converted into ethanol. While FIG. 5 illustrates a plurality of feedstock processing plants, it is also contemplated within the scope of the invention that only one feedstock processing plant may be employed in accordance with the present invention. In addition, while FIG. 5 identifies certain processes performed at the plurality of feedstock processing plants and other processes performed at the centrally-located ethanol producing plant, it is also contemplated within the scope of the invention that fewer or more processes may be performed at the plurality of feedstock processing plants and fewer or more processes may be performed at the centrally-located ethanol producing plant.

In use, several advantages of the disclosed embodiments of the method and system for producing ethanol are achieved. For example, the disclosed embodiments of the invention provide a method and system for producing ethanol that reduces the transportation costs associated with the production of ethanol from feedstock. The disclosed embodiments also provide a method and system that reduces the tonnage of feedstock transported from a feedstock provider to an ethanol producer. The disclosed embodiments further provide a method and system that produces byproducts that may be left at the site of the feedstock provider to be used as animal feed, animal bedding, compost, biofuel, chemicals or the like. In addition, the disclosed embodiments provide a method and system that produces a non-hazardous material to be transported from the feedstock provider to the ethanol producer. The disclosed embodiments also provide a method and system that reduces the storage requirements at the feedstock processor plants and the ethanol producer plant. The disclosed embodiments further provide a method and system that reduces or eliminates the environmental impact caused by the storage of feedstock, the disposal of byproducts, waste products and waste water, and the transportation of feedstock to an ethanol producing plant. The disclosed embodiments still further provide a method and system that reduces the size and cost of an ethanol producing plant and improve the efficiency of such a plant.

In addition, the disclosed embodiments provide a method and system that utilizes largely untapped resources as feedstock. The feedstock utilized by the disclosed embodiments is more abundant, less costly to produce and contains greater potential energy than feedstock that is more commonly utilized in the production of ethanol. The disclosed embodiments provide a method and system that allows feedstock providers to utilize the byproducts of the feedstock processing and derive revenue from feedstock sources that have traditionally been treated as waste.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. A method for producing sugar from woody feedstock, at one or more portable feedstock processing units, each of which is located at or near a woody feedstock provider, and the method comprising the steps of:
   (a) providing a woody feedstock comprising cellulose, hemicellulose, or lignocellulose;
   (b) processing the cellulose, hemicellulose, or lignocellulose of the woody feedstock at the one or more portable feedstock processing units, each of which is located at or near the woody feedstock provider, to produce sugar in a solution;
   wherein the processing comprises:
   (i) reducing the size of the woody feedstock to uniform 0.2 mm or smaller pieces;
   (ii) adding water to the woody feedstock to produce a slurry of 10-30% w/v solids;
   (iii) treating the slurry for no more than 20 minutes at 120° C. −180° C. to produce a first liquid fraction containing C5 sugars and a first solid fraction;
   (iv) removing and concentrating the first liquid fraction;
   (v) hydrolyzing the first liquid fraction with at least one hemicellulase enzyme;
   (vi) treating the first solid fraction at a temperature greater than 190° C. for greater than 5 minutes in a 1-3% acid solution to produce a mixture;
   (vii) neutralizing the mixture;

(viii) hydrolyzing the mixture with cellulase enzymes to produce a second liquid fraction containing C6 sugars and a second solid fraction; and (ix) separating the second liquid fraction from the second solid fraction;

(c) concentrating the sugar in the solution; and (d) transporting the concentrated sugar to a centralized plant for processing the concentrated sugar into biofuels or chemicals.

2. The method of claim 1, wherein the woody feedstock comprises wood chips, slash, wood, bark, sawdust, paper, poplars, willows, pulp, waste, or a combination thereof.

3. The method of claim 1, wherein the woody feedstock provider is a timber harvesting site or a mill.

4. The method of claim 1, wherein the processing is performed at a plurality of portable feedstock processing units.

5. The method of claim 4, wherein the plant for processing the concentrated sugar into biofuels or chemicals is centrally located relative to the plurality of portable feedstock processing units.

6. The method of claim 1, wherein the sugar comprises glucose.

7. The method of claim 1, wherein the sugar comprises xylose.

* * * * *